United States Patent
Bryant et al.

(10) Patent No.: US 7,144,887 B2
(45) Date of Patent: Dec. 5, 2006

(54) SUBSTITUTED 1,2,3-TRIAZOLO[1,5-A]QUINAZOLINES FOR ENHANCING COGNITION

(75) Inventors: Helen Jane Bryant, Roydon (GB); Mark Stuart Chambers, Puckeridge (GB); Philip Jones, Bishop Stortford (GB); Angus Murray MacLeod, Bishop Stortford (GB); Robert James Maxey, Amersham (GB)

(73) Assignee: Merck Sharp & Dohme Ltd., Hoddesdon (GB)

( * ) Notice: Subject to any disclaimer, the term of this patent is extended or adjusted under 35 U.S.C. 154(b) by 532 days.

(21) Appl. No.: 10/149,852

(22) PCT Filed: Dec. 11, 2000

(86) PCT No.: PCT/GB00/04752

§ 371 (c)(1),
(2), (4) Date: Jun. 14, 2002

(87) PCT Pub. No.: WO01/44250

PCT Pub. Date: Jun. 21, 2001

(65) Prior Publication Data

US 2003/0125333 A1   Jul. 3, 2003

(30) Foreign Application Priority Data

Dec. 14, 1999   (GB) .................... 9929569.3

(51) Int. Cl.
*A61K 471/04* (2006.01)
*A61K 31/505* (2006.01)
*C07D 239/00* (2006.01)
*C07D 471/00* (2006.01)
*C07D 487/00* (2006.01)

(52) U.S. Cl. ............... 514/257; 514/267; 544/251
(58) Field of Classification Search ........ 514/257, 514/267, 258; 544/251, 247, 252, 263
See application file for complete search history.

(56) References Cited

U.S. PATENT DOCUMENTS 4,788,186 A   11/1988 Occelli et al. ......... 514/210.21
5,306,819 A   4/1994 Albaugh et al. ............ 544/346
6,337,331 B1 *   1/2002 Broughton et al. ......... 514/257
6,730,681 B1 *   5/2004 Chambers et al. ....... 514/262.1

FOREIGN PATENT DOCUMENTS

| DE | 19617862 | 10/1997 |
| WO | WO 98/04559 | 2/1998 |
| WO | WO 98/50385 | 11/1998 |
| WO | 99/65907 | * 12/1999 |

OTHER PUBLICATIONS

G. Tarzia et al.: Benzodiazepine receptor ligand. Farmaco Ed. Sci. vol. 43, No. 2, 1988, pp. 189-201.
T.C. Porter et al.: "Tetrazolo [1,5-a]quinolines . . . " SYNTHESIS, No. 7, 1997, pp. 773-777.
G. Biagi et al.: "1,2,3-Triazolo[1,5-a]quinazolines . . . " FARMACO, vol. 51, No. 2, 1996, pp. 131-136.
L. Bertelli et al.: "Substituted 1,2,3-triazolo[2,5-a]quinazolines . . . " Eur. J. Med. Chem., vol. 35, 2000, pp. 333-341.

* cited by examiner

Primary Examiner—James O. Wilson
Assistant Examiner—Tamthom N. Truong
(74) Attorney, Agent, or Firm—John C. Todaro; Melvin Winokur

(57) ABSTRACT

The present invention provides a compound of formula (I) in which $R^1$ is generally hydrogen or $CF_3$, $R^2$ is generally hydrogen, W is a cyclic amine, a heterocycle or a group L-Y—X where L-Y is a linking portion and X is generally an aromatic or non-aromatic heterocycle, alkyl or alkylcarbonyl and Z is generally a heterocycle such as 5-methylisoxazol-3-yl, and pharmaceutically acceptable salts thereof for enhancing cognition in conditions such as Alzheimer's Disease, pharmaceutical compositions comprising them, their use for manufacturing medicaments and methods of treatment using them (I)

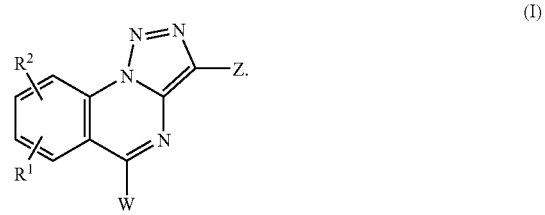

7 Claims, No Drawings

SUBSTITUTED 1,2,3-TRIAZOLO[1,5-A]QUINAZOLINES FOR ENHANCING COGNITION

CROSS REFERENCE TO RELATED APPLICATIONS

This application is a U.S. National Phase application under 35 U.S.C. § 371 of PCT Application No. PCT/GB00/04752, filed Dec. 11, 2000, which claims priority under 35 U.S.C. § 119 from GB Application No. 9929569.3, filed Dec. 14, 1999.

The present invention relates to a class of substituted triazolo-quinazoline derivatives and to their use in therapy. More particularly, this invention is concerned with substituted 1,2,3-triazolo[1,5-a]quinazoline derivatives which are ligands for $GABA_A$ receptors containing the α5 subunit and are therefore useful in therapy where cognition enhancement is required.

Receptors for the major inhibitory neurotransmitter, gamma-aminobutyric acid (GABA), are divided into two main classes: (1) $GABA_A$ receptors, which are members of the ligand-gated ion channel superfamily; and (2) $GABA_B$ receptors, which may be members of the G-protein linked receptor superfamily. Since the first cDNAs encoding individual $GABA_A$ receptor subunits were cloned the number of known members of the mammalian family has grown to thirteen (six α subunits, three β subunits, three γ subunits and one δ subunit). It may be that further subunits remain to be discovered; however, none has been reported since 1993

Although knowledge of the diversity of the $GABA_A$ receptor gene family represents a huge step forward in our understanding of this ligand-gated ion channel, insight into the extent of subtype diversity is still at an early stage. It has been indicated that an α subunit, a β subunit and a γ subunit constitute the minimum requirement for forming a fully functional $GABA_A$ receptor expressed by transiently transfecting cDNAs into cells. As indicated above, a δ subunit also exists, but is apparently uncommon in the native receptor.

Studies of receptor size and visualisation by electron microscopy conclude that, like other members of the ligand-gated ion channel family, the native $GABA_A$ receptor exists in pentameric form. The selection of at least one α, one β and one γ subunit from a repertoire of thirteen allows for the possible existence of more than 10,000 pentameric subunit combinations. Moreover, this calculation overlooks the additional permutations that would be possible if the arrangement of subunits around the ion channel had no constraints (i.e. there could be 120 possible variants for a receptor composed of five different subunits).

Receptor subtype assemblies which do exist include α1β2γ2, α2β2/3γ2, α3βγ2/3, α2βγ1, α5β3γ2/3, α6βγ2, α6βδ and α4βδ. Subtype assemblies containing an α1 subunit are present in most areas of the brain and account for over 40% of $GABA_A$ receptors in the rat. Subtype assemblies containing α2 and α3 subunits respectively account for about 25% and 17% of $GABA_A$ receptors in the rat. Subtype assemblies containing an α5 subunit are primarily hippocampal and represent about 4% of receptors in the rat.

A characteristic property of some $GABA_A$ receptors is the presence of a number of modulatory sites, of which the most explored is the benzodiazepine (BZ) binding site through which anxiolytic drugs such as diazepam and temazepam exert their effect. Before the cloning of the $GABA_A$ receptor gene family, the benzodiazepine binding site was historically subdivided into two subtypes, BZ1 and BZ2, on the basis of radioligand binding studies. The BZ1 subtype has been shown to be pharmacologically equivalent to a $GABA_A$ receptor comprising the α1 subunit in combination with β2 and γ2. This is the most abundant $GABA_A$ receptor subtype, representing almost half of all $GABA_A$ receptors in the brain.

A number of dementing illnesses such as Alzheimer's disease are characterised by a progressive deterioration in cognition in the sufferer. It would clearly be desirable to enhance cognition in subjects desirous of such treatment, for example for subjects suffering from a dementing illness.

It has been reported by McNamara and Skelton in Psychobiology, 21:101–108, that the benzodiazepine receptor inverse agonist β-CCM enhanced spatial learning in the Morris watermaze. However, β-CCM and other conventional benzodiazepine receptor inverse agonists are proconvulsant which makes it clear that they cannot be used as cognition enhancing agents in humans.

However, we have now discovered that it is possible to obtain medicaments which have cognition enhancing effects which may be employed with less risk of proconvulsant effects previously described with benzodiazepine receptor partial or full inverse agonists.

It has now been discovered that use of an α5 receptor partial or full inverse agonist which is relatively free of activity at α1 and/or α2 and/or α3 receptor binding sites can be used to provide a medicament which is useful for enhancing cognition but in which proconvulsant activity is reduced or eliminated. Inverse agonists at α5 which are not free of activity at α1 and/or α2 and/or α3 but which are functionally selective for α5 can also be used. Inverse agonists which are both selective for α5 and are relatively free of activity at α1, α2 and α3 receptor binding sites are preferred.

Biagi et al., in II Farmaco, 1996, 51, 137–140, describe the synthesis of inter alia 3-phenyl-5-methoxy-1,2,3-triazolo[1,5-a]quinazoline, which is stated therein to be a benzodiazepine receptor partial agonist agent. There is, however, no disclosure nor any suggestion in that publication of replacing the methoxy substituent in the 5-position with a moiety of the type denoted by W herein.

WO 98/50385 discloses substituted 1,2,4-triazolo[3,4-a]pyridazines which are $GABA_A$ receptor ligands selective for the α5 binding sites, but there is no disclosure nor any suggestion therein of compounds according to the present invention.

The present invention provides a compound of the formula (I):

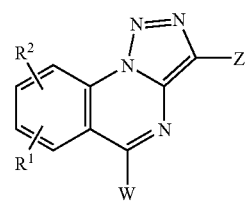

wherein:

R[1] is hydrogen, halogen or CN or a group $C_{1-4}$alkyl, $C_{2-4}$alkenyl, $C_{2-4}$alkynyl, $C_{1-4}$alkoxy, $C_{2-4}$alkenyloxy or $C_{2-4}$alkynyloxy, each of which groups is unsubstituted or substituted with one or two halogen atoms or with a pyridyl or phenyl ring each of which rings may be unsubstituted or independently substituted by one or two halogen atoms or nitro, cyano, amino, methyl or $CF_3$ groups;

$R^2$ is hydrogen, halogen or CN or a group $C_{1-4}$alkyl, $C_{2-4}$alkenyl, $C_{2-4}$alkynyl, $C_{1-4}$alkoxy, $C_{2-4}$alkenyloxy or $C_{2-4}$alkynyloxy each of which groups is unsubstituted or substituted with one or two halogen atoms;

W is selected from:
(i) a cyclic amine containing from 4 to 7 ring atoms,
  (a) one of which is nitrogen which is the point of attachment to the rest of the molecule,
  (b) another of which is optionally nitrogen, oxygen or sulphur
  (c) when the optional nitrogen atom is present then, optionally fused to this atom and an adjacent carbon atom of the cyclic amine, is an aromatic ring containing 5 or 6 atoms, 1–4 of which are nitrogen and the remainder carbon,
  (d) the cyclic amine is optionally substituted by an oxo group,
  (e) the cyclic amine, and any fused aromatic ring present, is optionally substituted by up to three substitutents, chosed from: $C_{1-4}$alkyl; $C_{2-4}$alkenyl; $C_{2-4}$alkynyl; halogen; $CF_3$hydroxy; hydroxy$C_{1-4}$alkyl; $C_{1-4}$alkylcarbonyl; $C_{1-4}$alkoxycarbonyl; $C_{1-4}$alkoxy; $NR^{10}R^{11}$ or $(CH_2)_rNR^{10}R^{11}$ where $R^{10}$ and $R^{11}$ are independently chosen from hydrogen, $C_{1-4}$alkyl, and $C_{1-4}$alkylcarbonyl and r is an integer from 1 to 4; $C_{1-4}$alkylcarbonyl; $C_{1-4}$alkoxycarbonyl; aminocarbonyl; and $(CH_2)_xU$ where x is an integer from zero to four and U is an aromatic group chosen from phenyl, a six-membered aromatic ring containing one or two nitrogen atoms and a five-membered aromatic ring containing 1, 2, 3 or 4 nitrogen atoms, U being optionally substituted with up to three substituents chosen from halogen, hydroxy, amino, $C_{1-4}$alkoxy, $C_{1-4}$alkyl and $C_{1-4}$hydroxyalkyl;
(ii) a five-membered heteroaromatic ring containing 1, 2, 3 or 4 nitrogen heteroatoms chosen from oxygen, nitrogen and sulphur, at most one of the heteroatoms being oxygen or sulphur, or a six-membered heteroaromatic ring containing one or two nitrogen atoms; the heteroaromatic ring being optionally fused to a pyridine or phenyl ring; the heteroaromatic ring and any fused ring present being optionally substituted by up to two groups chosen from hydroxy, halogen, amino, $C_{1-4}$alkyl and $C_{1-4}$alkoxy;
(iii) L—Y—X wherein L is O, $(CH)_2$, $(CH_2)_2$, S or $NR''$ where $R''$ is H, $C_{1-6}$alkyl, $C_{1-4}$alkoxy$C_{1-4}$alkyl or $C_{3-6}$cycloalkyl;

Y is a bond or optionally branched $C_{1-4}$alkylene or Y is a group $(CH_2)_jO$ or $(CH_2)_jNR^{12}$ or $(CH_2)_jNR^{12}C_{1-2}$alkylene, j is 2, 3 or 4 and $R^{12}$ is hydrogen or $C_{1-4}$alkyl and Y is optionally substituted by an oxo group; and X is a 5-membered heteroaromatic ring containing 1, 2, 3 or 4 heteroatoms independently chosen from oxygen, nitrogen and sulphur, at most one of the heteroatoms being oxygen or sulphur, or a 6-membered heteroaromatic ring containing 1, 2 or 3 nitrogen atoms, the 5- or 6-membered heteroaromatic ring being optionally fused to a benzene, pyridinyl, pyrimidinyl, pyrazinyl, pyridazinyl, piperidinyl, piperazinyl, morpholinyl or thiomorpholinyl ring and the heteroaromatic ring, including any fused portion, is optionally substituted by $R^x$ and/or $R^y$ and/or $R^z$, where $R^x$ is halogen, $C_{1-4}$alkoxy$C_{1-4}$alkenyl, OH, $R^3$, $OR^3$, $OCOR^3$, $COR^3$, $NR^4R^5$, $CONR^4R^5$, tri($C_{1-6}$alkyl)silyl$C_{1-6}$alkoxy$C_{1-4}$alkyl, CN or $R^9$, $R^y$ is halogen, $R^3$, $OR^3$, $OCOR^3$, $NR^4R^5$, $CONR^4R^5$ or CN and $R^z$ is $R^3$, $OR^3$ or $OCOR^3$, where $R^3$ is $C_{1-6}$alkyl, $C_{2-6}$alkenyl, $C_{2-6}$alkynyl, $C_{3-6}$cycloalkyl, hydroxy$C_{1-6}$alkyl and $R^3$ is optionally mono, di- or tri-fluorinated, $R^4$ and $R^5$ are each independently hydrogen, $C_{1-6}$alkyl, $C_{2-6}$alkenyl, $C_{2-6}$alkynyl, $C_{3-6}$cycloalkyl or $CF_3$ or, where possible, $R^4$ and $R^5$, together with a nitrogen atom to which they are commonly attached, form a 4–7 membered heteroaliphatic ring containing the said nitrogen atom and optionally one other heteroatom selected from O, N and S, which heteroaliphatic ring is optionally substituted by $C_{1-4}$alkyl, and $R^9$ is benzyl or an aromatic ring containing either 6 atoms, 1, 2 or 3 of which are optionally nitrogen, or 5 atoms, 1, 2 or 3 of which are independently chosen from oxygen, nitrogen and sulphur, at most one of the atoms being oxygen or sulphur, and $R^9$ is optionally substituted by one, two or three substituents independently chosen from halogen atoms and $C_{1-4}$alkyl, $C_{2-4}$alkenyl, $C_{2-4}$alkynyl, $C_{1-4}$alkoxy, $C_{2-4}$alkenyloxy and $C_{2-4}$alkynyloxy groups each of which groups is unsubstituted or substituted by one, two or three halogen atoms, and when X is a pyridine derivative, the pyridine ring is optionally in the form of the N-oxide and providing that when X is a tetrazole derivative it is substituted by a $C_{1-4}$alkyl group; or X is phenyl optionally substituted by one, two or three groups independently selected from halogen, cyano, $C_{1-6}$alkyl, $C_{2-6}$alkenyl, $C_{2-6}$alkynyl and $C_{3-6}$cycloalkyl; or X is $C_{1-4}$alkyl or $C_{1-4}$alkylcarbonyl; or X is a heteroaliphatic ring containing five or six atoms with one or two atoms chosen from oxygen, nitrogen and sulphur, which ring is optionally substituted by an oxo group, the ring being optionally fused to a benzene ring, and the ring being optionally substituted by halogen, $C_{1-4}$alkyl, $C_{1-4}$alkoxy or $C_{1-4}$alkoxycarbonyl;

Z is a 5-membered heteroaromatic ring containing 1, 2 or 3 heteroatoms independently selected from oxygen, nitrogen and sulphur, at most one of the heteroatoms being oxygen or sulphur and providing that when one of the atoms is oxygen or sulphur then at least one nitrogen atom is present, or a 6-membered heteroaromatic ring containing 2 or 3 nitrogen atoms, Z being optionally substituted by $R^v$ and/or $R^w$, where $R^v$ is halogen, $R^6$, $NR^7R^8$, $NR^7COR^8$, CN, furyl, thienyl, phenyl, benzyl, pyridyl or a 5-membered heteroaromatic ring containing at least one nitrogen atom and optionally 1, 2 or 3 other heteroatoms independently selected from oxygen, nitrogen and sulphur, at most one of the other heteroatoms being oxygen or sulphur and $R^w$ is $R^6$ or CN;

$R^6$ is $C_{1-6}$alkyl, $C_{2-6}$alkenyl, $C_{2-6}$alkynyl, $C_{3-6}$cycloalkyl, hydroxy$C_{1-6}$alkyl, $C_{1-6}$alkoxy, $C_{2-6}$alkenyloxy, $C_{2-6}$alkynyloxy, $CH_2F$ or $CF_3$; and $R^7$ and $R^8$ are each independently hydrogen, $C_{1-6}$alkyl, $C_{2-6}$alkenyl, $C_{2-6}$alkynyl, $C_{3-6}$cycloalkyl or $CF_3$ or $R^7$ and $R^8$, together with the nitrogen atom to which they are attached, form a 4–7 membered heteroaliphatic ring containing the nitrogen atom as the sole heteroatom;

or a pharmaceutically acceptable salt thereof.

As used herein, the expression "$C_{1-6}$alkyl" includes methyl and ethyl groups, and straight-chained and branched propyl, butyl, pentyl and hexyl groups. Particular alkyl groups are methyl, ethyl, n-propyl, isopropyl and t-butyl. Derived expressions such as "$C_{1-4}$alkyl", "$C_{2-4}$alkenyl", "$C_{2-6}$alkenyl", "hydroxy$C_{1-6}$alkyl", "$C_{2-4}$alkyl" and "$C_{2-6}$alkynyl" are to be construed in an analogous manner.

The expression "$C_{3-6}$cycloalkyl" as used herein includes cyclic propyl, butyl, pentyl and hexyl groups such as cyclopropyl and cyclohexyl.

As used herein, the expression "$C_{1-4}$alkylene" refers to alkanediyl groups of up to 4 carbon atoms wherein the unsatisfied valencies reside on the same carbon atom or on different carbon atoms.

Unless otherwise specified, 5- and 6-membered heteroaromatic rings shall include pyridinyl, pyridazinyl, pyrimidinyl, pyrazinyl, pyrrolyl, furyl, thienyl, pyrazolyl, oxazolyl, isoxazolyl, thiazolyl, isothiazolyl, imidazolyl, oxadiazolyl, triazolyl and thiadiazolyl groups. A suitable 5-membered heteroaromatic ring containing four nitrogen atoms is tetrazolyl. Suitable 6-membered heteroaromatic rings containing three nitrogen atoms include 1,2,4-triazine and 1,3,5-triazine. When a heteroaromatic ring comprises a hydroxy group as a substituent, and keto-enol tautomerism is possible, both tautomers are included within the scope of the invention. Thus, for example, a 3-hydroxy-1,2,4-triazole ring will be considered equivalent to a 3-oxo-1,2,4-triazole ring.

The term "halogen" as used herein includes fluorine, chlorine, bromine and iodine, of which fluorine and chlorine are preferred.

As used herein the term "$C_{1-6}$alkoxy" includes methoxy and ethoxy groups, and straight-chained, branched and cyclic propoxy, butoxy, pentoxy and hexoxy groups, including cyclopropylmethoxy. Derived expressions such as "$C_{2-6}$alkenyloxy", "$C_{2-6}$alkynyloxy", "$C_{1-4}$alkoxy", "$C_{2-4}$alkenyloxy" and "$C_{2-4}$alkyloxy" should be construed in an analogous manner.

In the compounds of formula I, $R^1$ is typically hydrogen, fluorine, chlorine, bromine or a group selected from $C_{1-4}$alkyl, $C_{2-4}$alkenyl, $C_{2-4}$alkynyl, or $C_{1-4}$alkoxy, each of which groups is unsubstituted or substituted with one or two halogen atoms or by a pyridyl or phenyl ring, each of which rings may be unsubstituted or substituted by one or two halogen atoms or nitro, cyano, amino, methyl or $CF_3$ groups. $R^1$ is preferably hydrogen, fluorine or pyridylmethoxy, most preferably hydrogen. In one embodiment $R^1$ is trifluoromethyl or hydrogen.

$R^2$ is typically hydrogen, fluorine, chlorine or bromine, and is preferably hydrogen or fluorine, most preferably hydrogen.

$R^3$ may be $C_{1-6}$alkyl, $C_{2-6}$alkenyl, $C_{2-6}$alkynyl, $C_{3-6}$cycloalkyl, or hydroxy$C_{1-6}$alkyl, any of which may be substituted by up to 3 fluorine atoms. Generally $R^3$ is $C_{1-4}$alkyl or $CF_3$. In particular $R^3$ is methyl or $CF_3$. $R^3$ may be tertiary butyl.

Generally, $R^4$ and $R^5$ are independently hydrogen or $C_{1-6}$alkyl, in particular hydrogen or methyl, for example both can be methyl.

Generally, $R^6$ is $CH_2F$, $CF_3$, $C_{1-6}$alkoxy, $C_{3-6}$cycloalkoxy, $C_{1-6}$alkyl or hydroxy$C_{1-6}$alkyl, for example, $CH_2F$, $CF_3$, methyl, ethyl, isopropyl, cyclopropyl, ethoxy or hydroxymethyl, particularly methyl, ethoxy or cyclopropyl.

Generally, $R^7$ and $R^8$ are independently hydrogen or $C_{1-6}$alkyl, particularly hydrogen or methyl.

Generally, $R^9$ is pyrazolyl, imidazolyl, phenyl, benzyl or pyridyl optionally substituted by halogen, preferably chlorine, or $CF_3$. In particular $R^9$ can be imidazol-1-yl, 3-trifluoromethylpyrid-5-yl, benzyl or 4-chlorophenyl.

$R^{10}$ and $R^{11}$ are particularly hydrogen, methyl or methylcarbonyl.

r is particularly two.

x is particularly zero or 1.

In one embodiment W is selected from:

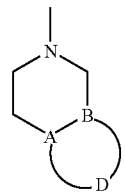

(i)

wherein A and B independently represent carbon or nitrogen, and D together with A and B completes a fused aromatic ring containing 5 or 6 atoms, 1–4 of which are nitrogen and the remainder carbon, optionally bearing up to two substituents selected from $C_{1-4}$alkyl, $C_{1-4}$alkoxy, halogen and $CF_3$;

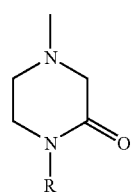

(ii)

wherein R represents H, $C_{1-4}$alkyl, phenyl or pyridyl, said phenyl and pyridyl groups optionally bearing up to three substituents selected from $C_{1-4}$alkyl, $C_{1-4}$alkoxy, halogen and $CF_3$; and (iii) L-Y—X wherein L is O, S or NR where RE is H, $C_{1-6}$alkyl or $C_{3-6}$cycloalkyl;

Y is optionally branched $C_{1-4}$alkylene optionally substituted by an oxo group or Y is a group $(CH_2)_jO$ wherein the oxygen atom is nearest the group X and j is 2, 3 or 4; and X is a 5-membered heteroaromatic ring containing 1, 2, 3 or 4 heteroatoms independently chosen from oxygen, nitrogen and sulphur, at most one of the heteroatoms being oxygen or sulphur, or a 6-membered heteroaromatic ring containing 1, 2 or 3 nitrogen atoms, the 5- or 6-membered heteroaromatic ring being optionally fused to a benzene ring and the heteroaromatic ring being optionally substituted by $R^x$ and/or $R^y$ and/or $R^z$, where $R^x$ is halogen, OH, $R^3$, $OR^3$, $OCOR^3$, $NR^4R^5$, $NR^4R^5CO$, tri($C_{1-6}$alkyl)silyl$C_{1-6}$alkoxy$C_{1-4}$alkyl, CN or $R^9$, $R^y$ is halogen, $R^3$, $OR^3$, $OCOR^3$, $NR^4R^5$, $NR^4R^5CO$ or CN and $R^z$ is $R^3$, $OR^3$ or $OCOR^3$, where $R^3$ is $C_{1-6}$alkyl, $C_{2-6}$alkenyl, $C_{2-6}$alkynyl, $C_{3-6}$cycloalkyl, hydroxy$C_{1-6}$alkyl and $R^3$ is optionally mono, di- or tri-fluorinated, $R^4$ and $R^5$ are each independently hydrogen, $C_{1-6}$alkyl, $C_{2-6}$alkenyl, $C_{2-6}$alkynyl, $C_{3-6}$cycloalkyl or $CF_3$ or, where possible, $R^4$ and $R^5$, together with a nitrogen atom to which they are commonly attached, form a 4–7 membered heteroaliphatic ring containing the said nitrogen atom and optionally one other heteroatom selected from O, N and S, and $R^9$ is benzyl or an aromatic ring containing either 6 atoms, 1, 2 or 3 of which are optionally nitrogen, or 5 atoms, 1, 2 or 3 of which are independently chosen from oxygen, nitrogen and sulphur, at most one of the atoms being oxygen or sulphur, and $R^9$ is optionally substituted by one, two or three substituents independently chosen from halogen atoms and $C_{1-4}$alkyl, $C_{2-4}$alkenyl, $C_{2-4}$alkynyl, $C_{1-4}$alkoxy, $C_{2-4}$alkenyloxy and $C_{2-4}$alkynyloxy groups each of which groups is unsubstituted or substituted by one, two or three halogen atoms, and when X is a pyridine derivative, the pyridine ring is optionally in the form of the N-oxide and providing that when X is a tetrazole derivative it is substituted by a $C_{1-4}$alkyl group; or X is phenyl optionally substituted by one, two or three groups independently selected from halogen, cyano, $C_{1-6}$-alkyl, $C_{2-6}$alkenyl, $C_{2-6}$alkynyl and $C_{3-6}$cycloalkyl.

When W represents the group:

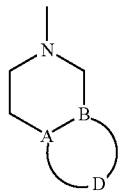

D together with A and B completes a fused 5- or 6-membered aromatic ring containing 1–4 nitrogen atoms, preferably 1–3 nitrogen atoms (including any nitrogen atom represented by A or B). Preferably, not more than one of A and B represents nitrogen. Suitable 5-membered aromatic rings formed by D together with A and B include imidazole, pyrazole, 1,2,3-triazole, 1,2,4-triazole and tetrazole, which are preferably unsubstituted or substituted by methyl or benzyl, particularly methyl. Suitable 6-membered aromatic rings formed by D together with A and B include pyridine, pyrazine and triazine. Preferred identities of W in this embodiment include

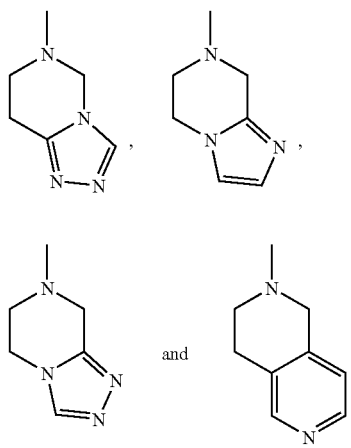

Other preferred identities include

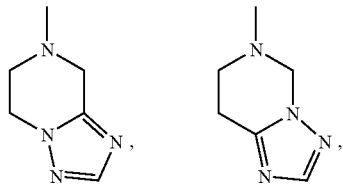

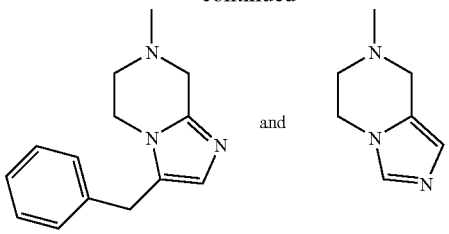

When X is a cyclic amine it is particularly piperidinyl, pyrrolidinyl, piperazinyl, azetidinyl, thiomorpholinyl or homopiperazinyl. It is optionally substituted by an oxo group, $NR^{10}R^{11}$, hydroxy, methylcarbonyl, $CH_2U$, U, methoxy, ethoxycarbonyl, hydroxymethyl and aminocarbonyl.

U is particularly phenyl, pyridyl or a triazole such as a 1,2,4-triazole.

Thus preferred values for W in this embodiment include: 5,6-dihydro[1,2,4]triazolo[4,5-a]pyrazin-7(8H)-yl, 5,6-dihydroimidazo[1,2-a]pyrazin-7(8H)-1-yl, 5,6-dihydro[1,2,4]triazolo[1,5-a]pyrazin-7(8H)-yl, 3-benzyl-5,6-dihydroimidazo[1,2-a]pyrazin-7(8H)-yl, 5,6-dihydroimidazo[1,5-a]pyrazin-7(8H)-yl, 7,8-dihydro[1,2,4]triaxolo[1,5-c]pyrimidin-6(5H)-yl, 3,4-dihydropyridino[3,4-c]pyridin-5(6H)-yl, 4-hydroxypiperidin-1-yl, 3-(N-acetyl-N-methylamino)pyrrolidin-1-yl, 4-oxopiperidin-1-yl, 4-(pyridin-2-yl)-3-oxopiperazin-1-yl, 4-phenyl-3-oxopiperazin-1-yl, 4-methyl-3-oxopiperazin-1-yl, 3-oxopiperazin-1-yl, 4-(pyrid-3-yl)-3-oxopiperazin-1-yl, thiomorpholin-4-yl, 4-(4-methyl-1,2,4-triazol-3-yl)-piperidin-1-yl, 4-(pyrid-2-ylmethyl)-3-oxopiperazin-1-yl, 3-methoxyazetidin-1-yl, 3-hydroxyazetidin-1-yl, 1,4-diazepan-5-on-1-yl, 4-(2-dimethylaminoethyl)-1,4-diazepan-5-on-1-yl, morpholin-4-yl, 4-hydroxymethylpiperidin-1-yl, 4-ethoxycarbonylpiperazin-1-yl, 3-oxopiperazin-1-yl, 2(R)-hydroxymethylpyrrolindin-1-yl, 3-hydroxymethylpiperazin-1-yl, 4-aminocarbonylpiperidin-1-yl, 4-methoxypiperidin-1-yl, 4-(pyrid-2-yl)piperazin-1-yl, 4-(pyrid-4-yl)piperazin-1-yl, 4-tertbutoxycarbonylpiperazin-1-yl, 4-(pyridin-3-yl)piperazin-3-on-1-yl, piperazin-1-yl, 4-(pyridin-3-yl)piperazin-1-yl, 4-(4-methoxypyridin-2-yl)piperazin-1-yl, 4-(3,5-dichloropyridin-4-yl)piperazin-1-yl; 4-dimethylaminopiperazin-1-yl, 3-hydroxypyrrolidin-1-yl and 4-acetoxypiperazin-1-yl.

When W represents the group:

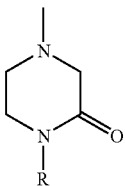

R may represent H, $C_{1-4}$alkyl, phenyl or pyridyl Said phenyl or pyridyl may bear up to three substituents selected from $C_{1-4}$alkyl, $C_{1-4}$alkoxy, halogen and $CF_3$, especially methyl, methoxy, chloro, fluoro or $CF_3$, but are preferably unsubstituted. Preferably, R represents H, methyl, phenyl, 2-pyridyl, 3-pyridyl or 2-methylpyridyl. Thus R may be hydrogen, methyl, phenyl, 2-pyridyl or 3-pyridyl.

When W is a heteroaromatic ring it is preferably a pyridine, imidazole, furan, triazole, pyrrole, pyrazole, pyridine, thiophene or pyridazine optionally fused to a pyridine ring, optionally substituted by $C_{1-4}$alkyl such as methyl.

Particular W groups in this embodiment include: imidazo[4,5-c]pyridin-1-yl, imidazo[4,5-b]pyridin-1-yl, imidazol-1-yl, 1,2,4-triazol-1-yl, pyrrol-1-yl, pyrazol-1-yl, fur-2-yl, pyridin-2-yl, thiophen-2-yl, pyridazin-4-yl, pyridin-3-yl, 1-methylimidazol-2-yl and 1-methyl-1,2,3-triazol-4-yl.

When W represents L-Y—X, L is preferably $(CH)_2$, $(CH_2)_2$, an oxygen atom or $NR''$, particularly an oxygen atom or $NR''$, in which $R''$ is preferably hydrogen or methyl. L may be $NR''$ L may be O. $R''$ may be hydrogen.

Apt values for Y include $CH_2$, $CH(CH_3)$, $CH_2CH_2$ and $CH_2CH_2CH_2$ optionally substituted by an oxo group, and $CH_2CH_2O$ and $CH_2CH_2CH_2O$. Other apt values are $CH_2CH_2NH$, $CH_2CO$ and $CH_2CON(CH_3)CH_2$. For example, Y can be $CH_2$, $CH_2CH_2$, $CH_2CH_2CH_2$, $CH_2CH_2O$ or $CH_2CH_2CH_2O$. Preferably Y is $CH_2$ or $CH_2CH_2$ and most preferably $CH_2$.

X may be methyl or methylcarbonyl.

X is generally: pyridyl, pyrazinyl, pyridazinyl or pyrimidinyl optionally substituted by one or more of $R^x$, $R^y$ and $R^z$ and optionally fused to a benzene ring; a 5-membered heteroaromatic ring containing 2 or 3 heteroatoms chosen from oxygen, sulphur and nitrogen, at most one of the heteroatoms being oxygen or sulphur, which is unsubstituted or substituted by one or more of $R^x$, $R^y$ and $R^z$; or phenyl optionally substituted by one, two or three independently chosen halogen atoms When X is a 6-membered heteroaromatic ring, $R^x$ is preferably absent or is halogen, $R^3$, $OR^3$, $NR^4R^5$ or $R^9$, and is more preferably absent or is methyl, $CF_3$, methoxy, bromine, chlorine, isopropoxy, or dimethylamino; and $R^y$ and $R^z$ are preferably absent.

When X is a 5-membered heteroaromatic ring, $R^x$ is preferably absent or is halogen, OH, $R^3$ or $R^9$, and more preferably $R^x$ is absent or is methyl, $CF_3$, OH, or chlorine; and $R^y$ and/or $R^z$ are absent or are independently halogen or $R^3$, especially methyl, $CF_3$ or chlorine. The substituent may be methoxymethylene or tertbutoxycarbonyl.

X may be a 1,3-dioxolan, piperazine or pyrrolidine, which is optionally substituted by an oxo group, optionally fused to a benzene ring and optionally mono substituted by methyl, halogen or butoxycarbonyl.

In particular X is pyridyl, or N-oxypyridyl which is unsubstituted or substituted by methyl, $CF_3$, methoxy, bromine, chlorine, isopropoxy, or dimethylamino, and X is optionally fused to a benzene ring; or X is pyrazolyl, isothiazolyl, isoxazolyl, 1,2,4-triazolyl, thiazolyl, 1,2,3-triazolyl, oxadiazolyl or imidazolyl which is unsubstituted or substituted by one or two groups independently chosen from methyl, $CF_3$, OH and chlorine; or X is phenyl which is unsubstituted or substituted by chlorine. X may be monosubstituted by tri($C_{1-6}$alkyl)silyl$C_{1-6}$alkoxy$C_{1-4}$alkyl such as trimethylsilylethoxymethyl. X may be bound to Y at any ring position available for such bonding. X may be fused to or substituted by piperazine which may be monosubstituted by tertbutoxycarbonyl or methyl.

Preferred embodiments of X comprise a ring selected from the group consisting of pyridine, pyridine N-oxide, 1,2,4-triazole, 1,2,3-triazole, isoxazole and oxadiazole. Specific values of X include 1-methyl-1,2,4-triazol-3-yl, 2-methyl-1,2,4-triazol-3-yl, 1-methyl-1,2,3-triazol-4-yl, pyridin-2-yl, pyridin-3-yl, N-oxypyridin-3-yl, isoxazol-3-yl, isoxazol-5-yl, 3-oxo-2H, 4H-1,2,4-triazol-5-yl and 3-methyl-1,2,5-oxadiazol-4-yl. Further preferred values of X are 1,3-dioxolan-2-yl, pyrrolid-2-on-1-yl, 1,3-dioxolan-2-on-4-yl, pyrazol-3-yl, 4-tert-butoxycarbonylpiperazin-1-yl, piperazin-1-yl, pyrazol-1-yl, thiazol-4-yl, 2-methyl-1,2,3-triazol-4-yl, 1,5-dimethylpyrazol-3-yl, imidazo[1,2-b]pyridin-2-yl, 2,3-dihydroindol-2-on-3-yl, 1,2,4-triazol-3-yl, pyridin-4-yl, 5,6-dihydro-7-tertbutoxycarbonyl-8H[1,2,4]triazol[1,5-a]pyrazol-2-yl, 5,6,7,8-tetrahydro[1,2,4]-triazolo[1,5-a]pyrazol-2-yl, 2-morpholin-4-yl)pyridin-6-yl, thiazol-2-yl, 2-(4-methylpiperazin-1-yl)pyridin-6-yl, thiazol-5-yl, 2-trifluoromethylpyridin-2-yl, 4-trifluoromethylpyridin-2-yl, 3-trifluoromethylpyridin-2-yl, 5-trifluoromethylisoxazol-3-yl, 2-trifluoromethylpyridin-3-yl, 1-methyl-3-trifluoromethylpyrazol-5-yl, 3-trifluoromethylpyrazol-4-yl and 4-trifluoromethylpyridin-3-yl.

A particularly preferred substituent for X is trifluoromethyl.

From the foregoing it will be understood that particularly suitable groups L-Y—X are $OCH_2X$, $NHCH_2X$ and $N(CH_3)CH_2X$ groups wherein X comprises a pyridine, pyridine N-oxide, isoxazole, oxadiazole or triazole ring.

Suitable values for Z include pyrimidinyl, pyrazinyl, pyrrolyl, oxazolyl, isoxazolyl, thiazolyl, isothiazolyl, oxadiazolyl and thiadiazolyl groups, which groups are optionally substituted by $R^v$ and/or $R^w$.

$R^v$ is suitably chlorine, $R^6$, thienyl, furyl, pyridyl or $NR^7R^8$, more particularly $R^6$, thienyl, furyl, pyridyl or $NR^7R^8$. Typical examples of $R^v$ are $C_{1-6}$alkyl, $C_{1-6}$alkoxy, $C_{3-6}$cycloalkyl, hydroxy$C_{1-6}$alkyl, pyridyl, thienyl or amino, more particularly methyl, ethyl, ethoxy, isopropyl, cyclopropyl, thienyl or pyridyl, and even more particularly methyl, ethyl, isopropyl, cyclopropyl or ethoxy. A further example of $R^v$ is chlorine.

$R^w$ is suitably $R^6$, for example $C_{1-6}$alkyl, $CH_2F$ or hydroxy$C_{1-6}$alkyl, more particularly methyl, $CH_2F$ or hydroxymethyl. Generally, $R^w$ is absent.

Z is very aptly a 5-membered heteroaromatic ring containing one oxygen and one or two nitrogen ring atoms, optionally substituted by a group $R^6$. In such compounds $R^6$ is favourably a methyl group.

Favoured values for Z include optionally substituted isoxazoles and oxadiazoles.

Z may be unsubstituted. Z may be substituted by trifluoromethyl.

Z may very aptly be substituted by methyl.

Particular values of Z include 5-methylisoxazol-3-yl.

A preferred subclass of compounds is that represented by formula Ia:

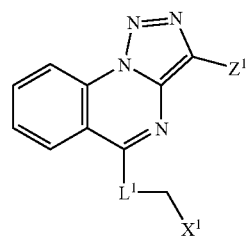

Ia wherein:

$X^1$ is a heteroaromatic ring selected from the group consisting of pyridine, pyridine N-oxide, 1,2,4-triazole, 1,2, 3-triazole, isoxazole and oxadiazole which is unsubstituted or substituted by $C_{1-4}$alkyl, $C_{3-6}$cycloalkyl, $C_{1-4}$alkoxy, OH, $CF_3$, or chlorine;

$L^1$ is O, NH or $NCH_3$; and $Z^1$ is an isoxazole optionally substituted by $C_{1-6}$alkyl, $C_{3-6}$cycloalkyl, hydroxy$C_{1-6}$alkyl or $C_{1-6}$alkoxy;

and pharmaceutically acceptable salts thereof.

$X^1$ is preferably 2-pyridyl, 3-pyridyl, N-oxy-3-pyridyl, 2-methyl-1,2,4-triazol-5-yl, 1-methyl-1,2,4-triazol-5-yl, 1-methyl-1,2,3-triazol-4-yl, isoxazol-3-yl, isoxazol-5-yl, 3-methyl-1,2,5-oxadiazol-4-yl or 3-oxo-1,2,4-triazol-5-yl.

$Z^1$ is preferably unsubstituted or substituted by methyl, $CH_2OH$ or $CH_2F$, in particular by methyl. $Z^1$ is particularly 5-methylisoxazol-3-yl.

Specific compounds within the scope of this embodiment of the invention include:

3-(5-methylisoxazol-3-yl)-5-(1-methyl-[1H]-1,2,4-triazol-3-ylmethoxy)-1,2,3-triazolo[1,5-a]quinazoline;

3-(5-methylisoxazol-3-yl)-5-(2-methyl-[2H]-1,2,4-triazol-3-ylmethoxy)-1,2,3-triazolo[1,5-a]quinazoline;

3-(5-methylisoxazol-3-yl)-5-(1-methyl-[1H]-1,2,3-triazol-4-ylmethoxy)-1,2,3-triazolo[1,5-a]quinazoline;

3-(5-methylisoxazol-3-yl)-5-(pyridin-2-ylmethoxy)-1,2,3-triazolo[1,5-a]quinazoline;

3-(5-methylisoxazol-3-yl)-5)-(pyridin-3-ylmethoxy)-1,2,3-triazolo[1,5-a]quinazoline;

3-(5-methylisoxazol-3-yl)-5-(N-oxypyridin-3-ylmethoxy)-1,2,3-triazolo[1,5-a]quinazoline;

3-(5-methylisoxazol-3-yl)-5-[N-methyl-N-(2-methyl-[2H]-1,2,4-triazol-3-ylmethyl)amino]-1,2,3-triazolo[1,5-a]quinazoline;

3-(5-methylisoxazol-3-yl)-5-[N-methyl-N-(1-methyl-[1H]-1,2,4-triazol-3-ylmethyl)amino]-1,2,3-triazolo[1,5-a]quinazoline;

3-(5-methylisoxazol-3-yl)-5-[(2-methyl-[2H]-1,2,4-triazol-3-ylmethyl)amino]-1,2,3-triazolo[1,5-a]quinazoline;

3-(5-methylisoxazol-3-yl)-5-[(1-methyl-[1H]-1,2,4-triazol-3-ylmethyl)amino]-1,2,3-triazolo[1,5-a]quinazoline;

3-(5-methylisoxazol-3-yl)-(pyridin-2-ylmethylamino)-1,2,3-triazolo[1,5-a]quinazoline;

5-(isoxazol-3-ylmethylamino)-3-(5-methylisoxazol-3-yl)-1,2,3-triazolo[1,5-a]quinazoline;

5-[(3-methyl-1,2,5-oxadiazol-4-yl)methylamino]-3-(5-methylisoxazol-3yl)-1,2,3-triazolo[1,5-a]quinazoline;

5-(isoxazol-5-ylmethylamino)-3-(5-methylisoxazol-3-yl)-1,2,3-triazolo[1,5-a]quinazoline;

3-(5-methylisoxazol-3-yl)-5-[(5-oxo-[1H, 4H]-1,2,4-triazol-3-yl)methylamino]-1,2,3-triazolo[1,5-a]quinazoline;

3-(5-methylisoxazol-3-yl)-5-[(1-methyl-[1H]-1,2,3-triazol-4-yl)methylamino]-1,2,3-triazolo[1,5-a]quinazoline;

3-(5-methylisoxazol-3-yl)-5-[N-methyl-N-(1-methyl-[1H]-1,2,3-triazol-4-ylmethyl)amino]-1,2,3-triazolo[1,5-a]quinazoline;

and pharmaceutically acceptable salts thereof.

Another preferred subclass of compounds is that represented by formula Ib:

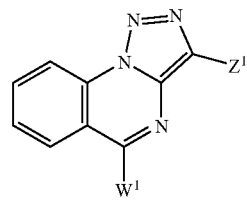

Ib wherein:

$W^1$ represents

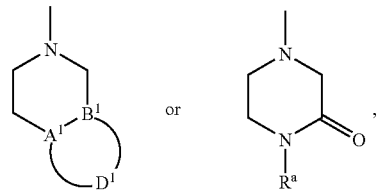

$A^1$ and $B^1$ independently represent nitrogen or carbon but are not both nitrogen;

$D^1$ together with $A^1$ and $B^1$ completes a fused triazole, pyrazole, imidazole or pyridine ring;

$R^a$ represents H, methyl, phenyl, 2-pyridyl, or 3-pyridyl; and $Z^1$ is as defined above;

and pharmaceutically acceptable salts thereof.

Preferably, $W^1$ represents

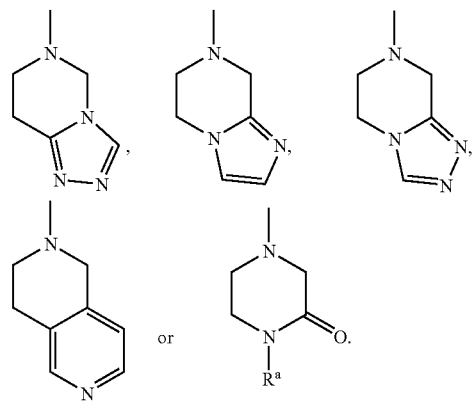

Specific compounds within the scope of this embodiment of the invention include:

4-[3-(5-methylisoxazol-3-yl)-[1,2,3]triazolo[1,5-a]quinazolin-5-yl]-1H-piperazin-2-one;

4-[3-(5-methylisoxazol-3-yl)-[1,2,3]triazolo[1,5-a]quinazolin-5-yl]-1-methylpiperazin-2-one;

4-[3-(5-methylisoxazol-3-yl)-[1,2,3]triazolo[1,5-a]quinazolin-5-yl]-1-phenylpiperazin-2-one;

4-[3-(5-methylisoxazol-3-yl)-[1,2,3]triazolo[1,5-a]quinazolin-5-yl]-1-(pyridin-2-yl)piperazin-2-one;

4-[3-(5-methylisoxazol-3-yl)-[1,2,3]triazolo[1,5-a]quinazolin-5-yl]-1-(pyridin-3-yl)piperazin-2-one;

5-(5,6-dihydro-8H-imidazo[1,2-a]pyrazin-7-yl)-3-(5-methylisoxazol-3-yl)-[1,2,3]triazolo[1,5-a]quinazoline;

5-(3,4-dihydro-1H-[2,6]naphthyridin-2-yl)-3-(5-methylisoxazol-3-yl)-[1,2,3]triazolo[1,5-a]quinazoline;

5-(5,6-dihydro-8H-[1,2,4]triazolo[4,3-a]pyrazin-7-yl)-3-(5-methylisoxazol-3-yl)-[1,2,3]triazolo[1,5-a]quinazoline;

and pharmaceutically acceptable salts thereof.

Where the compounds according to the invention have at least one asymmetric centre, they may accordingly exist as enantiomers. Where the compounds according to the invention possess two or more asymmetric centres, they may additionally exist as diastereoisomers. It is to be understood that all such isomers and mixtures thereof in any proportion are encompassed within the present invention.

It will be understood by the skilled person that when a five-membered heterocyclic ring is referred to in the foregoing as having four heteroatoms in the ring, then all these heteroatoms are nitrogen. It will further be understood that when a substituted five-membered heteroaromatic ring is referred to as having two nitrogen atoms and an oxygen or sulphur atom in the ring, then only one substituent may be present so that aromaticity is maintained. Thus, for example, in such a case X may be substituted only by $R^x$ and Z may be substituted only by $R^y$.

For use in medicine, the compounds of formula I may be in the form of pharmaceutically acceptable salts. Hence in a favoured aspect this invention provides the compounds of the formula I in the form of pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

The compounds of the present invention have a good binding affinity (Ki) for the α5 subunit of the $GABA_A$ receptor. In a preferred embodiment the compounds of the invention are binding selective for the α5 subunit relative to the α1, α2 and α3 subunits. In another preferred embodiment the compounds are functionally selective for the α5 subunit as partial or full inverse agonists whilst substantially being antagonists at the α1, α2 and α3 subunits.

The invention also provides pharmaceutical compositions comprising one or more compounds of this invention and a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, transdermal patches, auto-injector devices or suppositories; for oral, parenteral, intranasal, sublingual or rectal administration, or for administration by inhalation or insufflation. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums or surfactants such as sorbitan monooleate, polyethylene glycol, and other pharmaceutical diluents, e.g. water, to form a solid preformulation composition containing a homogeneous mixture of a compound of the present invention, or a pharmaceutically acceptable salt thereof When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. Typical unit dosage forms contain from 1 to 100 mg, for example 1, 2, 5, 10, 25, 50 or 100 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The present invention also provides a compound of the invention for use in a method of treatment of the human body. Preferably the treatment is for a condition associated with $GABA_A$ receptors comprising the α5 subunit and/or for the enhancement of cognition. Preferably the condition is a neurological deficit with an associated cognitive disorder such as a dementing illness such as Alzheimer's disease. Other conditions to be treated include cognition deficits due to traumatic injury, stroke, Parkinson's disease, Downs syndrome, age related memory deficits, attention deficit disorder and the like.

The present invention further provides the use of a compound of the present invention in the manufacture of a medicament for the enhancement of cognition, preferably in a human suffering from a dementing illness such as Alzheimer's disease.

Also disclosed is a method of treatment of a subject suffering from a cognition deficit, such as that resulting from a dementing illness such as Alzheimer's disease, which comprises administering to that subject an effective amount of a compound according to the present invention.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinyl-pyrrolidone or gelatin.

For the enhancement of cognition, a suitable dosage level is about 001 to 250 mg/kg per day, preferably about 0.01 to 100 mg/kg per day, and especially about 0.01 to 5 mg/kg of body weight per day. The compounds may be administered on a regimen of 1 to 4 times per day. In some cases, however, dosage outside these limits may be used.

The compounds in accordance with the invention may be prepared by a process which comprises the reaction of a compound of formula II with a compound of formula III:

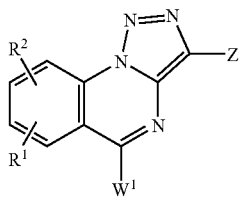

II

H—W

III wherein $R^1$, $R^2$, Z and W have the same meanings as before and $W^1$ is toluenesulphonyloxy. The reaction is typically carried out in an aprotic solvent such as DMSO in the presence of base at about 50° C. The compounds of formula II may be prepared by the reaction of a compound of formula IV with a compound of formula V, followed by conversion of the resulting intermediate VI to the tosylate II:

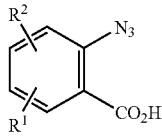

IV

NC—Z

V

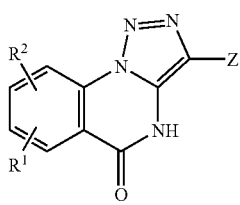

VI wherein $R^1$, $R^2$ and Z have the same meanings as before. The reaction between compounds IV and V is conveniently effected under basic conditions in a suitable solvent, for example sodium ethoxide in ethanol, typically at an elevated temperature. The compounds VI are converted to the tosylates II by reaction with toluenesulphonyl chloride in the presence of a base such as pyridine.

The intermediates IV may be prepared by diazotisation of a compound of formula VII:

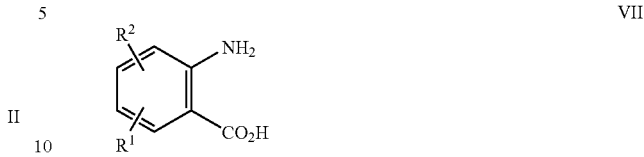

VII wherein $R^1$ and $R^2$ are as defined above, followed by displacement with azide ion The diazotisation/displacement procedure is conveniently effected by treating compound VII with sodium nitrite at 0° C. in the presence of a mineral acid, e.g. hydrochloric acid, then with sodium azide, typically in the presence of sodium acetate.

Alternatively, compounds of formula I in which W represents L-Y—X and L represents an oxygen atom may be prepared by reaction of a compound of formula VI with a compound of formula VIII:

VIII where X and Y are as defined above and G represents the moiety formed by reaction of a hydroxy group with triphenylphosphine in the presence of diethyl azodicarboxylate. The reaction between compounds VI and VIII is conveniently effected by stirring the reactants in a suitable solvent, e.g. tetrahydrofuran.

Where W is a heteroaromatic group compounds of formula I can be prepared by reacting a compound of formula II as defined above in which $W^1$ is chlorine or toluenesulphonyloxy with from 2 to 4 equivalents of a compound of formula IX:

W—SnBu$_3$    (IX)

wherein W is a five-membered heteroaromatic ring containing 1, 2, 3 or 4 nitrogen heteroatoms chosen from oxygen, nitrogen and sulphur, at most one of the heteroatoms being oxygen or sulphur, or a six-membered heteroaromatic ring containing one or two nitrogen atoms; the heteroaromatic ring being optionally fused to a pyridine or phenyl ring; the heteroaromatic ring and any fused ring present is optionally substituted by up to two groups chosen from hydroxy, halogen, amino, $C_{1-4}$alkyl and $C_{1-4}$alkoxy; generally in the presence of a catalyst such as Pd(PPh$_3$)$_4$, a salt such as CuI and in a solvent such as DMF, at about 70° C.

When L is (CH)$_2$ or (CH$_2$)$_2$ and Y is a bond the compounds of formula I are prepared by reacting a compound of formula II as defined above with Me$_3$SiCCH generally in the presence of a catalyst such as PdCl$_2$(PPh$_3$)$_2$, a salt such as CuI and a base such as Et$_3$N. The resulting compound is desilylated using TBAF in a solvent mixture such as dichloromethane with methanol. The resulting compound is iodinated, generally using sodium iodide in trifluoroacetic acid. The resulting compound is reacted with a compound of formula X:

X—SnBu$_3$    (X)

where X is as defined above, generally in the presence of a catalyst such as Pd(PPh$_3$)$_4$, a salt such as CuI and a solvent such as DMF, at a temperature of about 70° C., to give a compound of formula I wherein L is (CH)$_2$ and Y is a bond.

This compound is reduced with, for example, sodium borohydride in ethanol to give a compound of formula XI:

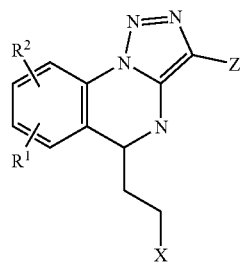

wherein R$^1$, R$^2$, X and Z are as defined above. The compound of formula XI is then selectively oxidised with, for example, DDQ generally in a solvent such as dichloromethane to give a compound of formula I in which L is (CH$_2$)$_2$ and Y is a bond.

Where they are not commercially available, the starting materials of formula III, V, VII, VIII, IX and X may be prepared by methods analogous to those described in the accompanying Examples, or by standard methods known from the art.

It will be understood that any compound of formula I initially obtained from the above processes may, where appropriate, subsequently be elaborated into a further compound of formula I by techniques known from the art. For example, a compound of formula I in which W contains a pyridine ring may be converted to the corresponding pyridine N-oxide by treatment with a suitable oxidising agent, such as m-chloroperoxybenzoic acid. Such a reaction may be carried out at ambient temperature in an aprotic solvent such as chloroform.

It will also be appreciated that where more than one isomer can be obtained from a reaction then the resulting mixture of isomers can be separated by conventional means.

Where the above-described process for the preparation of the compounds according to the invention gives rise to mixtures of stereoisomers, these isomers may be separated by conventional techniques such as preparative chromatography. The novel compounds may be prepared in racemic form, or individual enantiomers may be prepared either by enantiospecific synthesis or by resolution. The novel compounds may, for example, be resolved into their component enantiomers by standard techniques such as preparative HPLC, or the formation of diastereomeric pairs by salt formation with an optically active acid, such as (−)-di-p-toluoyl-d-tartaric acid and/or (+)-di-p-toluoyl-l-tartaric acid, followed by fractional crystallization and regeneration of the free base. The novel compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene & P. G. M. Wuts, Protective Groups in Organic Synthesis, John Wiley & Sons, 1991. The protecting groups may be removed at a convenient subsequent stage using methods known from the art.

The compounds in accordance with this invention potently inhibit the binding of [3H]-flumazenil to the benzodiazepine binding site of human GABA$_A$ receptors containing the α5 subunit stably expressed in Ltk. cells.

Reagents

Phosphate buffered saline (PBS).

Assay buffer: 10 mM KH$_2$PO$_4$, 100 mM KCl, pH 7.4 at room temperature.

[3H]-Flumazenil (18 nM for α1β3γ2 cells; 18 nM for α2β3γ2 cells; 10 nM for α3β3γ2 cells; 10 nM for α5β3γ2 cells) in assay buffer.

Flunitrazepam 100 μM in assay buffer.

Cells resuspended in assay buffer (1 tray to 10 ml).

Harvesting Cells

Supernatant is removed from cells. PBS (approximately 20 ml) is added. The cells are scraped and placed in a 50 ml centrifuge tube. The procedure is repeated with a further 10 ml of PBS to ensure that most of the cells are removed. The cells are pelleted by centrifuging for 20 min at 3000 rpm in a benchtop centrifuge, and then frozen if desired. The pellets are resuspended in 10 ml of buffer per tray (25 cm×25 cm) of cells.

Assay

Can be carried out in deep 96-well plates or in tubes. Each tube contains:

300 μl of assay buffer.

50 μl of [3H]-flumazenil (final concentration for α1β3γ2: 1.8 nM; for α2β3γ2: 1.8 nM; for α3β3γ2: 1.0 nM; for α5β3γ2: 1.0 nM).

0.50 μl of buffer or solvent carrier (e.g. 10% DMSO) if compounds are dissolved in 10% DMSO (total); test compound or flunitrazepam (to determine non-specific binding), 10 μM final concentration.

100 μl of cells.

Assays are incubated for 1 hour at 40° C., then filtered using either a Tomtec or Brandel cell harvester onto GF/B filters followed by 3×3 ml washes with ice cold assay buffer. Filters are dried and counted by liquid scintillation counting. Expected values for total binding are 3000–4000 dpm for total counts and less than 200 dpm for non-specific binding if using liquid scintillation counting, or 1500–2000 dpm for total counts and less than 200 dpm for non-specific binding if counting with meltilex solid scintillant. Binding parameters are determined by non-linear least squares regression analysis, from which the inhibition constant Ki can be calculated for each test compound.

The compounds of the accompanying Examples were tested in the above assay, and all were found to possess a Ki value for displacement of [3H]Ro 15-1788 from the α5 subunit of the human GABA$_A$ receptor of 100 nM or less, most were at 50 nM or less, many were at 10 nM or less and some were at 1 nM or less.

The compounds of the present invention can be shown to enhance cognition in the rat water maze test (Morris, Learning and Motivation, 1981, 12, 239ff). Further details of methodology for demonstrating that the present compounds enhance cognition can be found in WO-A-9625948.

The following Examples illustrate the present invention:

Intermediate 1

3-(5-Methylisoxazol-3-yl)-5-[(4-methyl)phenylsulphonyl]-[1,2,3]triazolo[1,5-a]quinazoline Step 1: 2-Azidobenzoic Acid A solution of sodium nitrite (4.75 g, 0.07 mol) in water (63 mL) was added dropwise to a stirred solution of anthranilic acid (10 g, 0.07 mol) in concentrated HCl (125 mL) and water (125 mL), maintaining the temperature below 5° C. After addition the mixture was stirred for 10 min then rapidly filtered. The solution was transferred to a dropping funnel and added dropwise to a solution of $NaN_3$ (4.2 g, 0.065 mol) and sodium acetate trihydrate (105 g, 0.77 mol) in water (125 mL). After addition the mixture was stirred at 0° C. for 15 min then at room temperature for 35 min. The suspension was filtered and washed with water. The solid was then dissolved in EtOAc, dried ($MgSO_4$) and the solvent evaporated. The title compound (52 g, 49%) was isolated as a cream solid. $^1$H NMR (360 MHz, $CDCl_3$) δ 7.24–7.29 (2H, m), 7.62 (1H, d of t, J=8.1 and 1.5 Hz), 8.12 (1H, d of d, J=7.7, and 1.6 Hz).

Step 2: 3-(5-Methylisoxazol-3-yl)-4H-[1,2,3]triazolo[1,5-a]quinazolin-5-one

Sodium (0.2 g, 8.6 mmol) was dissolved in EtOH (9 mL) and (5-methylisoxazol-3-yl)acetonitrile (0.65 g, 5.3 mmol) was added. The solution was stirred for 15 min then a solution of 2-azidobenzoic acid (0.7 g, 4.3 mmol) in EtOH (7 mL) was added and the mixture stirred for 1 h. After this time the mixture was heated at reflux for 5 h. The suspension was then allowed to cool to room temperature and the solvent removed in vacuo. The residue was taken up in water and 1N citric acid was added to pH4. The resultant precipitate was collected by filtration, washed with water then dried in vacuo at 60° C. The title compound (0.92 g, 80%) was isolated as a colourless solid. $^1$HNMR (360 MHz, $d_6$-DMSO) δ 2.51 (3H, s), 6.83 (1H, q, J=0.8 Hz), 7.72 (1H, d of t, J=8.1 and 1.0 Hz), 8.01 (1H, d of t, J=7.5 and 1.4 Hz), 8.24 (1H, dd, J=8.0 and 1.3 Hz), 8.36 (1H, d, J=8.0 Hz), 12.16 (1H, br s).

Step 3: 3-(5-Methylisoxazol-3-yl)-5-[(4-methyl)phenylsulphonyl]-[1,2,3]triazolo[1,5-a]quinazoline To a stirred solution of 3-(5-methylisoxazol-3-yl)-4H-[1,2,3]triazolo[1,5-a]quinazolin-5-one (0.92 g, 3.4 mmol) in DCM (30 mL) at 0° C. was added $Et_3N$ (0.95 mL, 6.9 mmol). After 10 min p-toluenesulphonyl chloride (1.32 g, 6.9 mmol) was added and the mixture stirred at room temperature overnight. The resultant solid was collected by filtration and washed with a little DCM. The tosylate (1.2 g, 82%) was isolated as a colourless solid. $^1$H NMR (360 MHz, $CDCl_3$) δ 2.47 (3H, s), 2.59 (3H, s), 6.71 (1H, s), 7.44 (2H, d, J=8.3 Hz), 7.76 (1H, t, J=8.1 Hz), 8.07 (1H, t, J=8.3 Hz) 8.31 (1H, d, J=8.1 Hz), 8.43 (2H, d, J=8.3 Hz), 8.68 (1H, d, J=8.4 Hz).

EXAMPLE 1

3-(5-Methylisoxazol-3-yl)-5-(1-methyl-1H-[1,2,4]triazol-3-ylmethoxy)-[1,2,3]triazolo[1,5-a]quinazoline To a solution of Intermediate 1 (100 mg, 0.24 mmol) and 3-hydroxymethyl-1-methyl-1,2,4-triazole (46 mg, 0.41 mmol) in DMF (3 mL) and THF (2 mL) at –78° C. was added lithium bis(trimethylsilyl)amide (0.44 ml of a 1M solution in THF, 0.44 mmol). After stirring at –78° C. for 30 min the cooling bath was removed and the mixture stirred at room temperature overnight. The solvent was evaporated and the residue partitioned between DCM (2×20 mL) and water (20 mL). The combined organic layers were dried ($MgSO_4$) and evaporated. The residue was chromatographed on silica gel, eluting with DCM:MeOH (100:0→90:10), to afford the title compound (38 mg, 44%) as a colourless solid. $^1$H NMR (360 MHz, $CDCl_3$) δ 2.55 (3H, s), 3.97 (3H, s), 5.82 (2H, s), 6.84 (1H, s), 7.66 (1H, t, J=7.4 Hz), 7.99 (1H, t, J=7.1 Hz), 8.08 (1H, s), 8.32 (1H, d, J=6.9 Hz), 8.65 (1H, d, J=7.0 Hz) MS ($ES^+$) 363 (M+1).

EXAMPLE 2

3-(5-Methylisoxazol-3-yl)-5-(2-methyl-2H-[1,2,4]triazol-3-ylmethoxy)-[1,2,3]triazolo[1,5-a]quinazoline In the same way as described in Example 1 using 3-hydroxymethyl-2-methyl-1,2,4-triazole, the title compound (63 mg, 60%) was isolated as a colourless solid. $^1$H NMR (360 MHz, $CDCl_3$) δ 2.54 (3H, s), 4.19 (3H, s), 5.92 (2H, s), 6.74 (1H, s), 7.71 (1H, t, J=8.3 Hz), 7.91 (1H, s), 8.03 (1H, t, J=8.5 Hz), 8.30 (1H, d, J=7.7 Hz), 8.66 (1H, d, J=7.7 Hz). MS ($ES^+$) 363 (M+1).

EXAMPLE 3

3-(5-Methylisoxazol-3-yl)-5-(1-methyl-1H-[1,2,3]triazol-4-ylmethoxy)-[1,2,3]triazolo[1,5-a]quinazoline In the same way as described in Example 1 using 4-hydroxymethyl-1-methyl-1,2,3-triazole, the title compound (71 mg, 68%) was isolated as a colourless solid. $^1$H NMR (360 MHz, $CDCl_3$) δ 2.57 (3H, s), 4.08 (3H, s), 5.83 (2H, s), 6.79 (1H, s), 7.68 (1H, t, J=7.2 Hz), 7.96 (1H, d of t, J=7.5 and 1.3 Hz), 8.29 (1H, d, J=7.5 Hz), 8.60 (1H, d, J=7.5 Hz), 8.80 (1H, s), MS ($ES^+$) 363 (M+1).

EXAMPLE 4

3-(5-Methylisoxazol-3-yl)-5-(pyridin-2-ylmethoxy)-[1,2,3]triazolo[1,5-a]quinazoline In the same way as described in Example 1 using 2-hydroxymethylpyridine, the title compound (28 mg, 30%) was isolated as a pale yellow solid. $^1$H NMR (360 MHz, $CDCl_3$) δ 2.55 (3H, s), 5.87 (2H, s), 6.74 (1H, s), 7.27–7.31 (1H, m), 7.68–7.80 (3H, m), 8.00 (1H, d of t, J=7.1 and 1.3 Hz), 8.36 (1H, d, J=7.9 Hz), 8.64–8.69 (2H, m). MS ($ES^+$) 359 (M+1).

EXAMPLE 5

3-(5-Methylisoxazol-3-yl)-5-(pyridin-3-ylmethoxy)-[1,2,3]triazolo[1,5-a]quinazoline In the same way as described in Example 1 using 3-hydroxymethylpyridine, the title compound (78 mg, 61%) was isolated as a pale yellow solid. $^1$H NMR (400 MHz, CDCl$_3$) δ 2.55 (3H, s), 5.79 (2H, s), 6.75 (1H, s), 7.36 (1H, dd, J=7.8 and 4.8 Hz), 7.70 (1H, d of t, J=8.2 and 1.0 Hz), 7.97–8.06 (2H, m), 8.27 (1H, dd, J=8.2 and 0.8 Hz), 8.62–8.65 (2H, m). MS (ES$^+$) 359 (M+1).

EXAMPLE 6

3-(5-Methylisoxazol-3-yl)-5-(1-oxypyridin-3-ylmethoxy)-[1,2,3]triazolo[1,5-a]quinazoline To a solution of 3-(5-methylisoxazol-3-yl)-5-(pyridin-3-ylmethoxy)-[1,2,3]triazolo[1,5-a]quinazoline (92 mg, 0.26 mmol) in DCM (12 mL) at 0° C. was added m-CPBA (164 mg of 75% purity; 0.71 mmol) over a 4 h period. After this time the solution was basified with 1N NaOH and the organic layer separated, dried (MgSO$_4$) and evaporated. The residue was triturated with EtOAc and the colourless solid (74 mg, 76%) collected by filtration. Found: C, 60.16; H, 3.80; N, 21.81%. Calc. C$_{19}$H$_{14}$N$_6$O$_3$.0.3 (H$_2$O): C, 60.09; H, 3.88; N, 22.13%. $^1$H NMR (400 MHz, CDCl$_3$) δ 2.55 (3H, s), 5.75 (2H, s), 6.74 (1H, s), 7.34 (1H, t, J=7.5 Hz), 7.65 (1H, d, J=7.8 Hz), 7.73 (1H, d of t, J=84 and 1.1 Hz), 8.03 (1H, d of t, J=7.3 and 1.2 Hz), 8.20 (1H, d, J=6.6 Hz), 8.28 (1H, d, J=8.3 Hz), 8.52 (1H, s), 8.66 (1H, d, J=8.1 Hz). MS (ES$^+$) 375 (M+1).

EXAMPLE 7

4-[3-(5-Methylisoxazol-3-yl)-[1,2,3]triazolo[1,5-a]quinazolin-5-yl]-1H-piperazin-2-one To a stirred suspension of Intermediate 1 (60 mg, 0.14 mmol) and Et$_3$N (40□L, 0.29 mmol) in DMSO (1 mL) at ambient temperature was added piperazin-2-one (15 mg, 0.15 mmol). The solution was warmed to 50° C. for 1 h then the heating ceased and water (10 mL) added. The resultant precipitate was filtered off, washed with water (2×10 mL) and EtOAc (2×10 mL). before vacuum oven drying to afford the title compound (45 mg, 92%) as a colourless solid. $^1$H NMR (400 MHz, d$_6$-DMSO) δ 2.51 (3H, s), 3.48–3.54 (2H, m), 3.93–3.98 (2H, m), 4.26 (2H, s), 6.86 (1H, s), 7.78 (1H, t, J=7.8 Hz), 8.07 (1H, t, J=7.7 Hz), 8.14 (1H, s), 8.24 (1H, d, J=8.1 Hz), 8.57 (1H, d, J=8.1 Hz). MS (ES$^+$) 350 (M+1). mp. 290° C. (dec).

EXAMPLE 8

4-[3-(5-Methylisoxazol-3-yl)-[1,2,3]triazolo[1,5-a]quinazolin-5-yl-1-methylpiperazin-2-one In the same way as described in Example 7 using 1-methylpiperazin-2-one (44 mg, 0.37 mmol), the title compound (38 mg, 74%) was isolated as a colourless solid. $^1$H NMR (400 MHz, d$_6$-DMSO) δ 2.51 (3H, s), 2.92 (3H, s), 3.62–3.65 (2H, m), 4.01–4.05 (2H, m), 4.32 (2H, s), 6.86 (1H, s), 7.78 (1H, t, J=8.2 Hz), 8.08 (1H, t, J=8.2 Hz), 8.23 (1H, d, J=8.3 Hz), 8.57 (1H, d, J=8.3 Hz). MS (ES$^+$) 364 (M+1). mp. 238° C. (dec).

EXAMPLE 9

4-[3-(5-Methylisoxazol-3-yl)-[1,2,3]triazolo[1,5-a]quinazolin-5-yl]-1-phenylpiperazin-2-one In the same way as described in Example 7 using 1-phenylpiperazin-2-one (40 mg, 0.23 mmol), the title compound (75 mg, 76%) was isolated as a colourless solid. $^1$H NMR (400 MHz, CDCl$_3$) δ 2.52 (3H, s), 4.07–4.10 (2H, m), 4.20–4.24 (2H, m), 4.62 (2H, s), 6.76 (1H, s), 7.30–7.36 (3H, m), 7.41–7.47 (2H, m), 7.70 (1H, t, J=8.9 Hz), 7.98 (1H, t, J=8.9 Hz), 8.11 (1H, d, J=8.4 Hz), 8.73 (1H, d, J=8.4 Hz). MS (ES$^+$) 426 (M+1). mp. 263° C. (dec).

EXAMPLE 10

4-[3-(5-Methylisoxazol-3-yl)-[1,2,3]triazolo[1,5-a]quinazolin-5-yl]-1-(pyridin-2-yl)piperazin-2-one

Step 1: 2-(2-Hydroxyethylamino)-N-pyridin-2-yl-acetamide

Following a published procedure (*Tetrahedron Lett.*, (1998), 39, 7459–7462) using 2-aminopyridine (2.0 g, 21 mmol), the title compound (0.17 g, 4%) was isolated as a colourless solid. $^1$H NMR (400 MHz, d$_6$-DMSO) δ 2.62 (2H, t, J=5.6 Hz), 2.70(1H, br s), 3.34 (2H, s), 3.44–3.50 (2H, m), 4.58 (1H, t, J=4.9 Hz), 7.09–7.13 (1H, m), 7.76–7.82 (1H, m), 8.10 (1H, d, J=8.3 Hz), 8.29–8.32 (1H, m), 10.20 (1H, br s). MS (ES$^+$) 196 (M+1). mp. 114–115° C.

Step 2: 1-(Pyridin-2-yl)piperazin-2-one

A stirred suspension of 2-(2-hydroxyethylamino)-N-pyridin-2-yl-acetamide (0.17 g, 0.87 mmol) under an inert atmosphere in THF (3 mL) was cooled to 0–5° C. Tributyl phosphine (0.32 mL, 1.15 mmol) was added followed by a solution of di-tert-butylazodicarboxylate (0.29 g, 1.23 mmol) in THF (3 mL) dropwise over 15 min. After a further 15 min. the mixture was warmed to 40° C. and a hydrogen chloride solution in diethylether (1M, 1.8 mL) added to produce a precipitate. The mixture was cooled to 0–5° C. and the solids filtered off to give a hydroscopic product. This was dissolved in MeOH—NH$_3$ and chromatographed on silica gel, eluting with DCM:MeOH (100:0 to 90:10), to afford the title compound (100 mg, 65%) as a colourless solid. $^1$H NMR (360 MHz, d$_6$-DMSO) δ 2.85 (1H, br s), 3.01 (2H, t, J=5.5 Hz), 3.44 (2H, s), 3.82 (2H, t, J=5.5 Hz), 7.17–7.22 (1H, m), 7.75–7.86 (2H, m), 8.41–8.45 (1H, m). MS (ES$^+$) 178 (M+1).

Step 3: 4-[3-(5-Methylisoxazol-3-yl)-[1,2,3]triazolo[1,5-a]quinazolin-5-yl]-1-(pyridin-2-yl)piperazin-2-one In the same way as described in Example 7 using 1-(pyridin-2-yl)piperazin-2-one (30 mg, 0.17 mmol), the title compound (20 mg, 33%) was isolated as a colourless solid. $^1$H NMR (400 MHz, d$_6$-DMSO) δ 2.52 (3H, s), 4.20–4.25 (2H, m), 4.28–4.33 (2H, m), 4.62 (2H, s), 6.90 (1H, s), 7.22–7.27 (1H, m), 7.79 (1H, t, J=8.3 Hz), 7.84–7.88 (1H, m), 7.97–8.01 (1H, m), 8.08 (1H, t, J=8.3 Hz), 8.34 (1H, d, J=7.9 Hz), 8.45–8.47 (1H, m), 859 (1H, d, J=7.9 Hz). MS (ES$^+$) 427 (M+1). mp. 266° C. (dec).

EXAMPLE 11

4-[3-(5-Methylisoxazol-3-yl)-[1,2,3]triazolo[1,5-a]
quinazolin-5-yl]-1-(pyridin-3-yl)piperazin-2-one

Step 1:
2-(2-Hydroxyethylamino)-N-pyridin-3-yl-acetamide

To a stirred solution of 3-aminopyridine (2.0 g, 21 mmol) and triethylamine (4 mL, 29 mmol) in THF (25 mL) under an inert atmosphere and precooled to 0–5° C., was added chloroacetyl chloride (2.2 mL, 26 mmol) dropwise over 10 min. After a further 15 min. the mixture was allowed to return to ambient temperature. Ethanolamine (5.4 mL, 87 mmol) was added and the dark solution warmed to 60° C. for 3 h. Solvents were removed in vacuo and DCM:MeOH (80:20) added to the resultant residue. This was filtered directly onto a column of silica gel, eluting with DCM:MeOH (90:10) to afford the title compound (1.3 g, 32%) isolated as an oil. $^1$H NMR (400 MHz, $d_6$-DMSO) δ 2.67 (2H, t, J=5.5 Hz), 3.32 (1H, br s), 3.40 (2H, s), 3.50 (2H, t, J=5.4 Hz), 4.70 (1H, br s), 7.33–7.37 (1H, m), 8.06–8.10 (1H, m), 8.26–8.28 (1H, m), 8.77–8.79 (1H, m), 10.20 (1H, br s). MS (ES$^+$) 196 (M+1).

Step 2: 1-(Pyridin-3-yl)piperazin-2-one

In the same way as described in Example 10, Step 1 using 2-(2-hydroxyethylamino)-N-pyridin-3-yl-acetamide (0.20 g, 1.02 mmol), the title compound (0.10 g, 55%) was isolated as an oily residue. $^1$H NMR (360 MHz, $d_6$-DMSO) δ 3.11 (2H, t, J=5.5 Hz), 3.30 (1H, br s), 3.49 (2H, s), 3.69 (2H, t, J=5.4 Hz), 7.42–7.47 (1H, m), 7.76–7.80 (1H, m), 8.42–8.45 (1H, m), 8.58 (1H, d, J=2.5 Hz). MS (ES$^+$) 178 (M+1).

Step 3: 4-[3-(5-Methylisoxazol-3-yl)-1,2,3]triazolo[1,5-a]quinazolin-5-yl]-1-(pyridin-3-yl)piperazin-2-one In the same way as described in Example 7 using 1-(pyridin-3-yl)piperazin-2-one (100 mg, 0.56 mmol), the title compound (40 mg, 67%) was isolated as a colourless solid. $^1$H NMR (400 MHz, $d_6$-DMSO) δ 2.51 (3H, s), 4.02–4.07 (2H, m), 4.20–4.26 (2H, m), 4.55 (2H, s), 6.88 (1H, s), 7.45–7.50 (1H, m), 7.80 (1H, t, J=8.3 Hz), 7.84–7.88 (1H, m), 8.10 (1H, t, J=7.8 Hz), 8.33 (1H, d, J=8.2 Hz), 8.45–8.49 (1H, m), 8.60 (1H, d, J=8.2 Hz), 8.65–8.67 (1H, m) MS (ES$^+$) 427 (M+1). mp. 247° C. (dec).

EXAMPLE 12

5-(5,6-Dihydro-8H-imidazo[1,2-a]pyrazin-7-yl)-3-(5-methylisoxazol-3-yl)-[1,2,3]triazolo[1.5-a]quinazoline

Step 1: (2-Chloroethyl)[1-(2-(trimethylsilyl)ethoxymethyl)-1H-imidazol-2-ylmethyl]amine A mixture of 2-chloroethylamine hydrochloride (8.23 g, 71 mmol), Et$_3$N (15.8 mL, 0.11 mol) and 1-(2-trimethylsilyl)ethoxymethyl-2-imidazolecarboxaldehyde (12.9 g, 57 mmol) in 1,2-DCE (400 mL) was heated at reflux under N$_2$ until all the solids went into solution. Sodium triacetoxyborohydride (15.0 g, 71 mmol) was then added portionwise over 15 min. The resulting solution was stirred at room temperature for 3 h, then poured into 1N NaOH solution (250 mL). The organics were extracted with EtOAc (3×200 mL) and the combined extracts washed with brine (150 mL), dried (MgSO$_4$), and concentrated under reduced pressure. The resulting crude residue was further purified by column chromatography on silica using 5% MeOH in DCM as the eluent, to yield the desired amine as a colourless oil (5.0 g, 30%). $^1$H NMR (360 MHz, CDCl$_3$) δ 0.00 (9H, s), 0.92 (2H, t, J=8.1 Hz), 2.99 (2H, t, J=6.0 Hz), 3.51 (2H, t, J=8.1 Hz), 3.62 (2H, t, J=6.0 Hz), 3.99 (2H, s), 5.35 (2H, s), 7.00 (2H, s). MS (ES$^+$) 290 (M+1).

Step 2: (2-Chloroethyl)[1-(2-(trimethylsilyl)ethoxymethyl)-1H-imidazol-2-ylmethyl]carbamic Acid Tert-Butyl Ester Di-tert-butyl dicarbonate (4.14 g, 19 mmol) was added portionwise over 2 min to a stirred solution of the foregoing amine (5.0 g, 17.3 mmol) in DCM (200 mL) at 0° C. under N$_2$. The resulting solution was stirred at 0° C. for 10 min and then warmed to room temperature and stirred for 1 h. The reaction mixture was concentrated under reduced pressure and then further purified by column chromatography on silica using 2% MeOH in DCM as the eluent to yield the desired amide (2.52 g, 34%). $^1$H NMR (360 MHz, CDCl$_3$) δ 0.00 (9H, s), 0.91 (2H, t, J=8.3 Hz), 1.47 (9H, s), 3.45–3.63 (6H, m), 4.68 (2H, s), 5.35 (2H, s), 6.98–7.08 (2H, m). MS (ES$^+$) 390 (M+1).

Step 3: 5,6-Dihydro-8H-imidazo[1,2-a]pyrazine-7-carboxylic Acid Tert-Butyl Ester Tetrabutylammonium fluoride (7.1 mL of a 1M solution in THF 7.1 mmol) was added to a solution of the carbamate (2.52 g, 6.5 mmol) in THF (50 mL) at RT under N$_2$. The resulting solution was heated at reflux for 1.5 h. Further tetrabutylammonium fluoride (7.1 mL of a 1M solution in THF 7.1 mmol) was added and heating was continued for a further 20 h. The reaction mixture was concentrated under reduced pressure and then purified by column chromatography twice on silica using 3% MeOH in DCM as the eluent to yield the desired piperazine (505 mg, 35%). $^1$H NMR (360 MHz, CDCl$_3$) δ 1.51 (9H, s), 3.84 (2H, t, J=5.6 Hz), 3.99 (2H, t, J=5.6 Hz), 4.69 (2H, s), 6.85 (1H, d, J=1.0 Hz), 7.03 (1H, d, J=1.0 Hz). MS (ES$^+$) 224 (M+1).

Step 4: 5,6,7,8-Tetrahydroimidazo[1,2-a]pyrazine, trifluoroacetic acid salt

A solution of the foregoing imidazo[1,2-a]pyrazine (505 mg, 2.26 mmol) in DCM (2.5 mL) was added to ice cold trifluoroacetic acid (5 mL) under N$_2$. The resulting mixture was stirred for 15 min at 0° C. and then warmed to room temperature and stirred for a further 45 min. The solvents were removed under reduced pressure and the resulting amine was used crude without further purification. $^1$H NMR (360 MHz, CDCl$_3$) δ 3.81 (2H, t, J=5.6 Hz), 4.52 (2H, t, J=5.6 Hz), 4.78 (2H, s), 7.65–7.70 (2H, m). MS (ES$^+$) 123 (M+H).

Step 5: 5-(5,6-Dihydro-8H-imidazo[1,2-a]pyrazin-7-yl)-3-(5-methylisoxazol-3-yl)-[1,2,3]triazolo[1.5-a]quinazoline A mixture of Intermediate 1 (75 mg, 0.178 mmol), the 5,6,7,8-tetrahydroimidazo[1,2-a]pyrazine, trifluoroacetic acid salt (42 mg, 0.178 mmol) and Et$_3$N (74 μL, 0.53 mmol) was heated in DMSO (5 mL) at 50° C. under N$_2$ for 45 min and then cooled to room temperature. $H_2O$ (30 mL) was added and the organics were extracted with DCM (3×30 mL). The combined extracts were washed with $H_2O$ (2×30 mL) and dried ($MgSO_4$) before being concentrated under reduced pressure. The crude material was dry loaded onto silica using MeOH/DCM and purified by column chromatography on silica using 3% MeOH in DCM as the eluent to yield the desired amidate (30 mg, 45%) which was recrystallised from DCM/EtOAc, m.p. 208–211° C. (decomp). $^1$H NMR (360 MHz, $CDCl_3$) δ 2.54 (3H, s), 4.26 (2H, t, J=5.4 Hz), 4.44 (2H, t, J=5,4 Hz), 5.03 (2H, s), 6.78 (1H, s), 7.10 (1H, d, J=1.5 Hz), 7.20 (1H, d, J=1.5 Hz), 7.82 (1H, t, J=8.0 Hz), 8.06 (1H, t, J=8.0 Hz), 8.29 (1H, d, J=8.0 Hz), 8.63 (1H, d, J=8.0 Hz). MS ($ES^+$) 373 (M+H).

EXAMPLE 13

5-(3,4-Dihydro-1H-[2,6]naphthyridin-2-yl)-3-(5-methylisoxazol-3-yl)-[1,2,3]triazolo[1,5-a]quinazoline Step 1:
N-Benzyl-3-(2-hydroxyethyl)-4-pyridinecarboxamide Butyl lithium (61.5 mL of a 1.6 M solution in hexane, 98.5 mmol) was added dropwise over 10 min to a stirred solution of N-benzyl-4-pyridinecarboxamide (9.94 g, 46.9 mmol) in THF (200 mL) at −78° C. under $N_2$. The reaction mixture immediately turned dark blue, and was stirred for 1 h. A solution of ethylene oxide (2.27 g, 51.6 mmol) in dioxane (10 mL) was then added and the resulting mixture stirred at −78° C. for 3 h, after which time it was warmed to room temperature and quenched with MeOH (40 mL). The quenched reaction mixture was poured into $H_2O$ (200 mL) and extracted with EtOAc (3×150 mL). The combined organic extracts were washed with brine (150 mL), dried ($MgSO_4$) and concentrated under reduced pressure. The crude material was purified by column chromatography on silica using 5–10% MeOH in DCM as the eluent to yield the desired alcohol (2.9 g, 24%). MS ($ES^+$) 257 (M+1).

Step 2:
2-Benzyl-3,4-dihydro-2H-[2,6]naphthyridin-1-one

Diethyl azodicarboxylate (1.83 mL, 11.6 mmol) was added dropwise over 3 min to a stirred solution of the foregoing alcohol (2.7 g, 10.6 mmol) and $PPh_3$ (3.05 g, 11.7 mmol) in THF (100 mL) at room temperature under $N_2$. The reaction mixture was stirred for 48 h and then $H_2O$ (100 mL) was added. The organics were extracted with DCM (100 mL) and then washed with $H_2O$ (100 mL) and brine (100 mL). The solution was dried ($MgSO_4$) and concentrated under reduced pressure. The crude residue was then purified by column chromatography on silica using 2% MeOH in EtOAc as the eluent to yield the desired amide (740 mg, 29%). $^1$H NMR (400 MHz, $CDCl_3$) δ 2.95 (2H, t, J=5.8 Hz), 3.53 (2H, t, J=5.8 Hz), 4.79 (2H, s), 5.19 (2H, s), 7.20–740 (5H, m), 7.90–8.00 (1H, m), 8.52 (1H, s), 8.60–8.70 (1H, m). MS ($ES^+$) 239 (M+1).

Step 3:
2-Benzyl-1.2,3.4-tetrahydro[2,6]naphthyridine

A solution of the lactam (740 mg, 3.11 mmol) in THF (5 mL) was added dropwise over 2 min to a stirred solution of $LiAlH_4$ (4.66 mmol) in THF (1.0 M, 4.66 mL) at room temperature under $N_2$. Upon complete addition the reaction was stirred at room temperature for 5 min and then heated at reflux for 2 h. The reaction mixture was cooled to room temperature and quenched with EtOAc (2 mL) and then 4N NaOH solution (20 mL). The resulting mixture was stirred for 15 min and then extracted with EtOAc (2×30 mL). Ammonia solution (20 mL) was then added to the aqueous fraction and this was extracted with EtOAc (30 mL). The combined organic extracts were concentrated under reduced pressure and used without further purification. $^1$H NMR (400 MHz, $CDCl_3$) δ 2.77 (2H, t, J=5.8 Hz), 2.88 (2H, t, J=5.8 Hz), 3.59 (2H, s), 3.70 (2H, s), 6.88 (1H, d, J=5 Hz), 7.20–7.38 (5H, m), 8.28 (1H, d, J=5.0 Hz), 8.34 (1H, s). MS ($ES^+$) 225 (M+1)

Step 4: 1,2,3,4-Tetrahydro[2,6]naphthyridine 1,4-Cyclohexadiene (5 mL) was added to a stirred mixture of the foregoing amine and 10% Pd on carbon (500 mg) in EtOH (6 mL) and AcOH (2 mL). The resulting mixture was heated at reflux for 2 h, then cooled to room temperature, filtered and concentrated under reduced pressure. The crude residue was purified by column chromatography on alumina using 0.5–2% MeOH in DCM (containing 1% $NH_3$ solution) to yield the secondary amine (180 mg, 43%). $^1$H NMR (400 MHz, $CDCl_3$) δ 2.78 (2H, d, J=5.8 Hz), 3.16 (2H, d, J=5.8 Hz), 3.99 (2H, s), 7.28(1H, d, J=5.0 Hz), 8.31(1H, d, J=5.0 Hz), 8.33 (1H, s). MS ($ES^+$) 135 (M+1).

Step 5: 5-(3,4-Dihydro-1H-[2,6]naphthyridin-2-yl)-3-(5-methylisoxazol-3-yl)-[1,2,3]triazolo[1,5-a]quinazoline A solution of Intermediate 1 (200 mg, 0.47 mmol), 1,2,3,4-tetrahydro[2,6]naphthyridine (90 mg, 0.67 mmol) and $Et_3N$ (171μL, 1.24 mmol) in DMSO (6 mL) was heated at 80° C. for 45 min and then cooled to room temperature. The undissolved solid was collected by filtration and then dissolved in DCM The organic layer was dried ($MgSO_4$) and evaporated to afford the title compound (102 mg, 56%) as a colourless solid. The filtrate was diluted with DCM (30 mL) and washed with water (20 mL). The organic layer was separated and the aqueous phase washed with more DCM (20 mL). The combined organic layers were washed with water (2×20 mL), dried ($MgSO_4$) and evaporated. The residue was triturated with ether to afford the title compound as a pale yellow solid (78 mg, 43%). $^1$H NMR (400 MHz, $CDCl_3$) δ) 2.55 (3H, S), 3.26–3.29 (2H, m), 4.00–4.03 (2H, m), 4.91 (2H, s), 6.74 (1H, s), 7.20 (1H, d, J=4.9 Hz), 769 (1H, t, J=7.8 Hz), 7.96 (1H, t, J=7.8 Hz), 8.09 (1H, d, J=8.2 Hz), 8.45 (1H, d, J=4.9 Hz), 8.52 (1H, s), 8.70 (1H, d, J=8.3 Hz). MS ($ES^+$) 384 (M+1).

EXAMPLE 14

5-(5,6-Dihydro-8H-[1,2,4]triazolo[4,3-a]pyrazin-7-yl)-3-(5-methylisoxazol-3-yl)-[1,2,3]triazolo[1,5-a]quinazoline Step 1:
5-Methoxy-3,6-dihydro-2H-pyrazine-1-carboxylic Acid Benzyl Ester $Na_2CO_3$ (45.3 g, 0.43 mol) was added in one portion to a stirred solution of benzyl 3-oxopiperazine-1-carboxylate (5 g, 21.4 mmol) in DCM (200 mL) at 0° C. under $N_2$. The resulting suspension was stirred at 0° C. for 10 min and then trimethyloxonium tetrafluoroborate (11.0 g, 74 mmol) was added in one portion. The resulting mixture was warmed to room temperature and stirred for 6 h before being poured into H₂O (200 mL) and separated. The aqueous layer was then extracted with DCM (200 mL). The combined organic extracts were washed with H₂O (3×100 mL) and brine (100 mL), dried and concentrated under reduced pressure. The crude residue was further purified by column chromatography on silica using 5% MeOH in DCM as the eluent to give the imino ether (2.5 g, 47%). ¹H NMR (360 MHz, CDCl₃) δ 2.99 (3H, s), 3.36 (2H, br, s), 3.72 (2H, t, J=5.4 Hz), 4.14 (2H, s), 5.14 (2H, s), 7.28–7.45 (5H, m).

Step 2: 5,6-Dihydro-8H-[1,2,4]triazolo[4,3-a]pyrazine-7-carboxylic Acid Benzyl Ester A solution of the iminoether (2.5 g, 10.1 mmol) and formyl hydrazide (1.21 g, 20.2 mmol) in EtOH (50 mL) were heated at reflux for 24 h. The reaction mixture was cooled to room temperature and concentrated under reduced pressure, the residue was taken up in DCM/MeOH, dry loaded onto silica and further purified by column chromatography on silica using 10% MeOH in DCM as the eluent to give the triazole (770 mg, 31%). ¹H NMR (360 MHz, CDCl₃) δ 3.85–3.96 (2H, m), 4.03–4.15 (2H, m), 4.91 (2H, s), 5.19 (2H, s), 7.25–7.43 (5H, m), 8.13 (1H, s). MS (ES⁺) 259 (M+1).

Step 3: 5,6,7,8-Tetrahydro[1,2,4]triazolo[4,3-a]pyrazine

30% HBr in AcOH (10 mL) was added to the carbamate (770 mg, 3.1 mmol) at room temperature and the resulting mixture was stirred for 4 h. The mixture was partially concentrated (to approximately 2 mL) under reduced pressure and H₂O added (10 mL). Solid NaOH was added to neutralise the solution. The solvent was removed under reduced pressure and then the crude residue azeotroped with toluene (3×40 mL). The mixture was dry loaded onto silica using MeOH and DCM and purified by column chromatography on silica using 20% MeOH in DCM (containing 1% NH₃ solution) as the eluent to give the triazolopiperazine (385 mg, Quant.). ¹H NMR (360 MHz, CDCl₃) δ 3.75 (2H, t, J=5.8 Hz), 4.45 (2H, t, J=5.8 Hz), 4.64 (2H, s), 8.62 (1H, s). MS (ES⁺) 125 (M+1).

Step 4: 5-(5,6-Dihydro-8H-[1,2,4]triazolo[4,3-a]pyrazin-7-yl)-3-(5-methylisoxazol-3-yl)-[1,2,3]triazolo[1,5-a]quinazoline The reaction was carried out as described in Example 12 using 5,6,7,8-tetrahydro[1,2,4]triazolo[4,3-a]pyrazine (25 mg, 0.20 mmol) and Intermediate 1 (85 mg, 0.20 mmol) to give a crude residue which was purified by column chromatography on silica using 2–5% MeOH in DCM (containing 1% NH₃ solution) as the eluent to yield the desired amidate (18 mg, 24%). ¹H NMR (400 MHz, d6-DMSO) δ 2.53 (3H, s), 4.14 (2H, t, J=5.4 Hz), 4.45 (2H, t, J=5, 4 Hz), 5.04 (2H, s), 687 (1H, s), 7.83 (1H, t, J=7.8 Hz), 8.11 (1H, t, J=7.8 Hz), 8.31 (1H, d, J=7.8 Hz), 8.58 (1H, s), 8.60 (1H, d, J=7.8 Hz). MS (ES⁺) 374 (M+H).

The following can be made by analogy with the preceding Examples or by following the general methodology described herein:

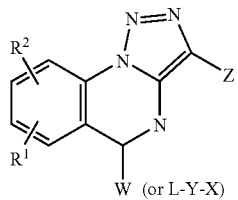

W (or L-Y-X)

| Example no. | R¹ | Rᵛ | W | L | Y | X |
|---|---|---|---|---|---|---|
| 15 | H | CH₃ | 5,6-dihydro[1,2,4]triazolo[1,5-a]pyrazin-7(8H)-yl | — | — | — |
| 16 | H | CH₃ | 7,8-dihydro[1,2,4]triazolo[1,5-c]pyrimidin-6(5H)-yl | — | — | — |
| 17 | H | CH₃ | 4-hydoxymethylpiperidin-1-yl | — | — | — |
| 18 | H | CH₃ | 3-(N-acetyl-N-methylamino)pyrrolidin-1-yl | — | — | — |
| 19 | H | CH₃ | piperidin-4-on-1-yl | — | — | — |
| 20 | H | CH₃ | 3-hydroxypyrrolidin-1-yl | — | — | — |
| 21 | H | CH₃ | 4-acetylpiperazin-1-yl | — | — | — |
| 22 | H | CH₃ | 3-benzyl-5,6-dihydroimidazo[1,2-a]pyrazin-7(8H)-yl | — | — | — |
| 23 | H | CH₃ | 5,6-dihydroimidazo[1,5-a]pyrazin-7(8H)-yl | — | — | — |
| 24 | H | CH₃ | thiomorpholin-4-yl | — | — | — |
| 25 | H | CH₃ | 4-(4-methyl-1,2,4-triazol-3-yl)piperidin-1-yl | — | — | — |
| 26 | H | CH₃ | — | NCH₂CH₂OCH₃ | CH₂CH₂O | CH₃ |
| 27 | H | CH₃ | — | NCH₃ | CH₂ | dioxolan-2-yl |
| 28 | H | CH₃ | — | NH | CH₂CH₂O | CH₃ |
| 29 | H | CH₃ | — | NH | CH₂CH₂NH | COCH₃ |
| 30 | H | CH₃ | 4-(pyrid-2-ylmethyl)piperazin-3-on-1-yl | — | — | — |
| 31 | H | CH₃ | 3-methoxyazetidin-1-yl | — | — | — |
| 32 | H | CH₃ | 3-hydroxyazetidin-1-yl | — | — | — |

-continued

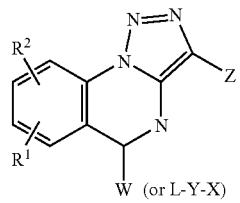
W (or L-Y-X)

| Example no. | R¹ | Rᵛ | W | L | Y | X |
|---|---|---|---|---|---|---|
| 33 | H | CH₃ | imidazo[4,5-c]pyridin-1-yl | — | — | — |
| 34 | H | CH₃ | — | O | CH₂CH₂O | CH₃ |
| 35 | H | CH₃ | imidazo[4,5-b]pyridin-1-yl | — | — | — |
| 36 | H | CH₃ | 1,4-diazepan-5-on-1-yl | — | — | — |
| 37 | H | CH₃ | — | O | CH₂CH₃ | pyrrolidin-2-on-1-yl |
| 38 | H | CH₃ | 4-(2-dimethylaminoethyl)-1,4-diazepan-5-on-1-yl | — | — | — |
| 39 | H | CH₃ | — | O | CH₂ | dioxolan-2-on-4-yl |
| 40 | H | CH₃ | morpholin-4-yl | — | — | — |
| 41 | H | CH₃ | 4-ethoxycarbonylpiperazin-1-yl | — | — | — |
| 42 | H | CH₃ | 4-hydroxymethylpiperidin-1-yl | — | — | — |
| 43 | H | CH₃ | — | O | bond | CH₃ |
| 44 | H | CH₃ | imidazol-1-yl | — | — | — |
| 45 | H | CH₃ | 1,2,4-triazol-1-yl | — | — | — |
| 46 | H | CH₃ | pyrrol-1-yl | — | — | — |
| 47 | H | CH₃ | pyrazol-1-yl | — | — | — |
| 48 | H | CH₃ | — | NH | — | pyrazol-3-yl |
| 49 | H | CH₃ | — | O | CH₂COO | CH₃ |
| 50 | H | CH₃ | — | O | CH₂CH₂CH₂ | CH₃ |
| 51 | H | CH₃ | 2R-hydroxymethylpyrrolidin-1-yl | — | — | — |
| 52 | H | CH₃ | 3-hydroxymethylpiperazin-1-yl | — | — | — |
| 53 | H | CH₃ | fur-2-yl | — | — | — |
| 54 | H | CH₃ | — | O | CH₂CO | 4-tert-butoxycarbonylpiperazin-1-yl |
| 55 | H | CH₃ | — | O | CH₂CONCH₃ | methyl |
| 56 | H | CH₃ | — | O | CH₂CON(CH₃)CH₂ | pyridin-3-yl |
| 57 | H | CH₃ | — | O | CH₂CO | piperazin-1-yl |
| 58 | H | CH₃ | pyridin-2-yl | — | — | — |
| 59 | H | CH₃ | thiophen-2-yl | — | — | — |
| 60 | H | CH₃ | pyridazin-4-yl | — | — | — |
| 61 | H | CH₃ | pyridin-3-yl | — | — | — |
| 62 | H | CH₃ | 4-aminocarbonylpiperidin-1-yl | — | — | — |
| 63 | H | CH₃ | 4-methoxypiperidin-1-yl | — | — | — |
| 64 | H | CH₃ | 1-methylimidazol-2-yl | — | — | — |
| 65 | H | CH₃ | 1-methyl-1,2,3-triazol-4-yl | — | — | — |
| 66 | H | CH₃ | — | CHCH | bond | pyridin-2-yl |
| 67 | H | CH₃ | — | CHCH | bond | 1-methyl-1,2,4-triazol-5-yl |
| 68 | H | CH₃ | — | NCH₃ | CH₂ | isoxazol-3-yl |
| 69 | H | CH₃ | — | NCH₃ | CH₂ | pyridin-3-yl |
| 70 | H | CH₃ | — | CH₂CH₂ | bond | pyridin-2-yl |
| 71 | H | CH₃ | — | CH₂CH₂ | bond | 1-methyl-1,2,4-triazol-5-yl |
| 72 | H | CH₃ | — | NH | CH₂CH₂ | pyrazol-1-yl |
| 73 | H | CH₃ | — | NH | CH₂ | thiazol-4-yl |
| 74 | H | CH₃ | — | NH | CH₂ | pyrazol-3-yl |
| 75 | H | CH₃ | — | CHCH | bond | 2-methyl-1,2,3-triazol-4-yl |
| 76 | H | CH₃ | — | NH | CH₂ | thiazol-5-yl |
| 77 | H | CH₃ | — | NH | CH₂ | thiazol-2-yl |
| 78 | H | CH₃ | — | NCH₃ | CH₂ | 3-methoxymethylpyrazol-5-yl |
| 79 | H | CH₃ | — | NH | CH₂ | 1,3-dimethylpyrazol-4-yl |
| 80 | H | CH₃ | — | Nh | CH₂ | 2,3-dimethylpyrazol-4-yl |
| 81 | H | CH₃ | imidazo[1,2-a]pyrimidin-2-yl | — | — | — |
| 82 | H | CH₃ | — | NH | CH₂ | 1,3-dihydro-2H-indol-2-on-3-yl |
| 83 | H | CH₃ | — | NH | CH₂ | 1,2,4-triazol-3-yl |
| 84 | H | CH₃ | 4-pyridin-2-ylpiperazin-1-yl | — | — | — |
| 85 | H | CH₃ | 4-pyridin-4-ylpiperazin-1-yl | — | — | — |
| 86 | H | CH₃ | 4-(tert-butoxycarbonyl)piperazin-1-yl | — | — | — |
| 87 | H | CH₃ | — | NH | CH₂ | pyridin-4-yl |

-continued

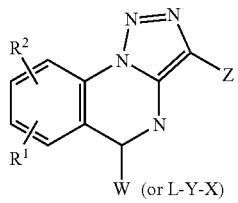

W (or L-Y-X)

| Example no. | R¹ | Rᵛ | W | L | Y | X |
|---|---|---|---|---|---|---|
| 88 | H | CH₃ | — | NH | CH₂ | pyridin-3-yl |
| 89 | H | CH₃ | piperazin-1-yl | — | — | — |
| 90 | H | CH₃ | 4-pyridin-3-ylpiperazin-1-yl | — | — | — |
| 91 | H | CH₃ | 5,6-dihydro-7(8H)-tert-butoxycarbonyl[1,2,4]triazolo[1,5-a]pyrazin-2-yl | — | — | — |
| 92 | H | CH₃ | 5,6,7,8-tetrahydro[1,2,4]triazolo[1,5-a]pyrazin-2yl | — | — | — |
| 93 | H | CH₃ | 4-(4-methoxypyridin-2-yl)piperazin-1-yl | — | — | — |
| 94 | H | CH₃ | 4-(3,5-dichloropyridin-4-yl)piperazin-1-yl | — | — | — |
| 95 | H | CH₃ | — | O | CH₂CH₂NH | pyridin-2-yl |
| 96 | H | CH₃ | — | O | CH₂CH₂NH | pyridin-4-yl |
| 97 | H | CH₃ | 4-dimethylaminopiperidin-1-yl | — | — | — |
| 98 | H | CH₃ | — | O | CH₂ | 2-morpholin-4-yl-pyridin-6-yl |
| 99 | H | CH₃ | — | O | CH₂ | 2-(4-methylpiperazin-1-yl)pyridin-6-yl |
| 100 | H | CH₃ | — | O | CH₂ | 3-trifluoromethylpyridin-2-yl |
| 101 | H | CH₃ | — | O | CH₂ | 4-trifluoromethylpyridin-2-yl |
| 102 | H | CH₃ | — | O | CH₂ | 3-trifluoromethylpyridin-6-yl |
| 103 | H | CH₃ | — | O | CH₂ | 5-trifluoromethylisoxazol-3-yl |
| 104 | H | CH₃ | — | O | CH₂ | 2-trifluoromethylpyridin-5-yl |
| 105 | H | CH₃ | — | O | CH₂ | 1-methyl-5-trifluoromethylpyrazol-3-yl |
| 106 | H | CF₃ | — | O | CH₂ | 3-trifluoromethylpyridin-6-yl |
| 107 | H | CF₃ | — | O | CH₂ | 4-trifluoromethylpyridin-2-yl |
| 108 | CF₃ | CH₃ | — | O | CH₂ | 1-methyl-1,2,4-triazol-5-yl |
| 109 | CF₃ | CH₃ | — | O | CH₂ | pyridin-3-yl |
| 110 | CF₃ | CH₃ | — | O | CH₂ | 3-trifluoromethylpyrid-6-yl |
| 111 | H | CF₃ | — | O | CH₂ | 1-methyl-1,2,4-triazol-5-yl |
| 112 | CF₃ | CH₃ | — | O | CH₂ | 4-trifluoromethylpyridin-2-yl |
| 113 | CF₃ | CH₃ | — | O | CH₂ | pyridin-2-yl |
| 114 | CF₃ | CH₃ | — | O | CH₂ | 1-methyl-1,2,3-triazol-4-yl |
| 115 | H | CF₃ | — | O | CH₂ | 1-methyl-1,2,4-triazol-3-yl |
| 116 | CF₃ | CH₃ | — | O | CH₂ | 1-methyl-3-trifluoromethylpyrazol-5-yl |
| 117 | H | CH₃ | — | O | CH₂ | 1-methyl-5-trifluoromethylpyrazol-4-yl |
| 118 | H | CH₃ | — | O | CH₂ | 4-trifluoromethylpyridin-3-yl |

The invention claimed is:
1. A compound of the formula (I):

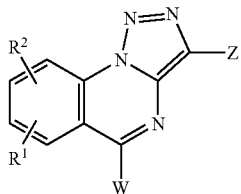

wherein:
R$^1$ is hydrogen, halogen or CN or a group C$_{1-4}$alkyl, C$_{2-4}$alkenyl, C$_{2-4}$alkynyl, C$_{1-4}$alkoxy, C$_{2-4}$alkenyloxy or C$_{2-4}$alkynyloxy, each of which groups is unsubstituted or substituted with one or two halogen atoms or with a pyridyl or phenyl ring each of which rings may be unsubstituted or independently substituted by one or two halogen atoms or nitro, cyano, amino, methyl or CF$_3$ groups;
R$^2$ is hydrogen, halogen or CN or a group C$_{1-4}$alkyl, C$_{2-4}$alkenyl, C$_{2-4}$alkynyl, C$_{1-4}$alkoxy, C$_{2-4}$alkenyloxy or C$_{2-4}$alkynyloxy each of which groups is unsubstituted or substituted with one or two halogen atoms;
W is selected from:
(i) a cyclic amine containing from 4 to 7 ring atoms,
  (a) one of which is nitrogen which is the point of attachment to the rest of the molecule,
  (b) another of which is optionally nitrogen, oxygen or sulphur
  (c) when the optional nitrogen atom is present then, optionally fused to this atom and an adjacent carbon atom of the cyclic amine, is an aromatic ring containing 5 or 6 atoms, 1–4 of which are nitrogen and the remainder carbon,
  (d) the cyclic amine is optionally substituted by an oxo group,
  (e) the cyclic amine, and any fused aromatic ring present, is optionally substituted by up to three substitutents, chosed from: C$_{1-4}$alkyl; C$_{2-4}$alkenyl; C$_{2-4}$alkynyl; halogen; CF$_3$; hydroxy; hydroxyC$_{1-4}$alkyl; C$_{1-4}$alkylcarbonyl; C$_{1-4}$alkoxycarbonyl; C$_{1-4}$alkoxy; NR$^{10}$R$^{11}$ or (CH$_2$)$_r$NR$^{10}$R$^{11}$ where R$^{10}$ and R$^{11}$ are independently chosen from hydrogen, C$_{1-4}$alkyl, and C$_{1-4}$alkylcarbonyl and r is an integer from 1 to 4; C$_{1-4}$alkylcarbonyl; C$_{1-4}$alkoxycarbonyl; aminocarbonyl; and (CH$_2$)$_x$U where x is an integer from zero to four and U is an aromatic group chosen from phenyl, a six-membered aromatic ring containing one or two nitrogen atoms and a five-membered aromatic ring containing 1, 2, 3 or 4 nitrogen atoms, U being optionally substituted with up to three substituents chosen from halogen, hydroxy, amino, C$_{1-4}$alkoxy, C$_{1-4}$alkyl and C$_{1-4}$hydroxyalkyl;
(ii) a five-membered heteroaromatic ring containing 1, 2, 3 or 4 heteroatoms chosen from oxygen, nitrogen and sulphur, at most one of the heteroatoms being oxygen or sulphur, or a six-membered heteroaromatic ring containing one or two nitrogen atoms; the heteroaromatic ring being optionally fused to a pyridine or phenyl ring; the heteroaromatic ring and any fused ring present being optionally substituted by up to two groups chosen from hydroxy, halogen, amino, C$_{1-4}$alkyl and C$_{1-4}$alkoxy;

(iii) L-Y—X wherein
L is O, (CH$_2$)$_2$, (CH$_2$)$_2$, S or NR″ where R″ is H, C$_{1-6}$alkyl, C$_{1-4}$alkoxyC$_{1-4}$alkyl or C$_{3-6}$cycloalkyl;
Y is a bond or optionally branched C$_{1-4}$alkylene or Y is a group (CH$_2$)$_j$O or (CH$_2$)$_j$NR$^{12}$ or (CH$_2$)$_j$NR$^{12}$C$_{1-2}$alkylene, j is 2, 3 or 4 and R$^{12}$ is hydrogen or C$_{1-4}$alkyl and Y is optionally substituted by an oxo group; and
X is a 5-membered heteroaromatic ring containing 1, 2, 3 or 4 heteroatoms independently chosen from oxygen, nitrogen and sulphur, at most one of the heteroatoms being oxygen or sulphur, or a 6-membered heteroaromatic ring containing 1, 2 or 3 nitrogen atoms, the 5- or 6-membered heteroaromatic ring being optionally fused to a benzene, pyridinyl, pyrimidinyl, pyrazinyl, pyridazinyl, piperidinyl, piperazinyl, morpholinyl or thiomorpholinyl ring and the heteroaromatic ring, including any fused portion, is optionally substituted by R$^x$ and/or R$^y$ and/or R$^z$, where R$^x$ is halogen, C$_{1-4}$alkoxyC$_{1-4}$alkenyl, OH, R$^3$, OR$^3$, OCOR$^3$, COR$^3$, NR$^4$R$^5$, CONR$^4$R$^5$, tri(C$_{1-6}$alkyl)silylC$_{1-6}$alkoxyC$_{1-4}$alkyl, CN or R$^9$, R$^y$ is halogen, R$^3$, OR$^3$, OCOR$^3$, NR$^4$R$^5$, CONR$^4$R$^5$ or CN and R$^z$ is R$^3$, OR$^3$ or OCOR$^3$, where R$^3$ is C$_{1-6}$alkyl, C$_{2-6}$alkenyl, C$_{2-6}$alkynyl, C$_{3-6}$cycloalkyl, hydroxyC$_{1-6}$alkyl and R$^3$ is optionally mono, di- or tri-fluorinated, R$^4$ and R$^5$ are each independently hydrogen, C$_{1-6}$alkyl, C$_{2-6}$alkenyl, C$_{2-6}$alkynyl, C$_{3-6}$cycloalkyl or CF$_3$ or, where possible, R$^4$ and R$^5$, together with a nitrogen atom to which they are commonly attached, form a 4–7 membered heteroaliphatic ring containing the said nitrogen atom and optionally one other heteroatom selected from O, N and S, which heteroaliphatic ring is optionally substituted by C$_{1-4}$alkyl, and R$^9$ is benzyl or an aromatic ring containing either 6 atoms, 1, 2 or 3 of which are optionally nitrogen, or 5 atoms, 1, 2 or 3 of which are independently chosen from oxygen, nitrogen and sulphur, at most one of the atoms being oxygen or sulphur, and R$^9$ is optionally substituted by one, two or three substituents independently chosen from halogen atoms and C$_{1-4}$alkyl, C$_{2-4}$alkenyl, C$_{2-4}$alkynyl, C$_{1-4}$alkoxy, C$_{2-4}$alkenyloxy and C$_{2-4}$alkynyloxy groups each of which groups is unsubstituted or substituted by one, two or three halogen atoms, and when X is a pyridine derivative, the pyridine ring is optionally in the form of the N-oxide and providing that when X is a tetrazole derivative it is substituted by a C$_{1-4}$alkyl group; or
X is phenyl optionally substituted by one, two or three groups independently selected from halogen, cyano, C$_{1-6}$alkyl, C$_{2-6}$alkenyl, C$_{2-6}$alkynyl and C$_{3-6}$cycloalkyl; or
X is C$_{1-4}$alkyl or C$_{1-4}$alkylcarbonyl; or
X is a heteroaliphatic ring containing five or six atoms with one or two atoms chosen from oxygen, nitrogen and sulphur, which ring is optionally substituted by an oxo group, the ring being optionally fused to a benzene ring, and the ring being optionally substituted by halogen, C$_{1-4}$alkyl, C$_{1-4}$alkoxy or C$_{1-4}$alkoxycarbonyl;
Z is a 5-membered heteroaromatic ring containing 1, 2 or 3 heteroatoms independently selected from oxygen, nitrogen and sulphur, at most one of the heteroatoms being oxygen or sulphur and providing that when one of the atoms is oxygen or sulphur then at least one nitrogen atom is present, or a 6-membered heteroaromatic ring containing 2 or 3 nitrogen atoms, Z being optionally substituted by R$^v$ and/or R$^w$, where R$^v$ is halogen, R$^6$, NR$^7$R$^8$, NR$^7$COR$^8$, CN, furyl, thienyl, phenyl, benzyl, pyridyl or a 5-membered heteroaromatic ring containing at least one nitrogen atom and optionally 1, 2 or 3 other heteroatoms independently selected from oxygen, nitrogen and sulphur, at most one of the other heteroatoms being oxygen or sulphur and $R^w$ is $R^6$ or CN;

$R^6$ is $C_{1-6}$alkyl, $C_{2-6}$alkenyl, $C_{2-6}$alkynyl, $C_{3-6}$cycloalkyl, hydroxy$C_{1-6}$alkyl, $C_{1-6}$alkoxy, $C_{2-6}$alkenyloxy, $C_{2-6}$alkynyloxy, $CH_2F$ or $CF_3$; and $R^7$ and $R^8$ are each independently hydrogen, $C_{1-6}$alkyl, $C_{2-6}$alkenyl, $C_{2-6}$alkynyl, $C_{3-6}$cycloalkyl or $CF_3$ or $R^7$ and $R^8$, together with the nitrogen atom to which they are attached, form a 4–7 membered heteroaliphatic ring containing the nitrogen atom as the sole heteroatom;

or a pharmaceutically acceptable salt thereof.

2. A compound according to claim 1 in which $R^1$ is hydrogen.

3. A compound according to claim 1 in which Z is substituted by trifluoromethyl.

4. A compound according to claim 1 in which Z is 5-methylisoxazol-3-yl.

5. A compound of the formula (I):

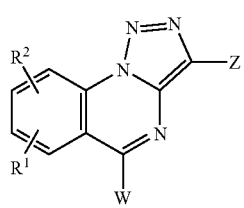

wherein:

$R^1$ is hydrogen, halogen or CN or a group $C_{1-4}$alkyl, $C_{2-4}$alkenyl, $C_{2-4}$alkynyl, $C_{1-4}$alkoxy, $C_{2-4}$alkenyloxy or $C_{2-4}$alkynyloxy, each of which groups is unsubstituted or substituted with one or two halogen atoms or with a pyridyl or phenyl ring each of which rings may be unsubstituted or independently substituted by one or two halogen atoms or nitro, cyano, amino, methyl or $CF_3$ groups;

$R^2$ is hydrogen, halogen or CN or a group $C_{1-4}$alkyl, $C_{2-4}$alkenyl, $C_{2-4}$alkynyl, $C_{1-4}$alkoxy, $C_{2-4}$alkenyloxy or $C_{2-4}$alkynyloxy each of which groups is unsubstituted or substituted with one or two halogen atoms;

Z is a 5-membered heteroaromatic ring containing 1, 2 or 3 heteroatoms independently selected from oxygen, nitrogen and sulphur, at most one of the heteroatoms being oxygen or sulphur and providing that when one of the atoms is oxygen or sulphur then at least one nitrogen atom is present, or a 6-membered heteroaromatic ring containing 2 or 3 nitrogen atoms, Z being optionally substituted by $R^v$ and/or $R^w$, where $R^v$ is halogen, $R^6$, $NR^7R^8$, $NR^7COR^8$, CN, furyl, thienyl, phenyl, benzyl, pyridyl or a 5-membered heteroaromatic ring containing at least one nitrogen atom and optionally 1, 2 or 3 other heteroatoms independently selected from oxygen, nitrogen and sulphur, at most one of the other heteroatoms being oxygen or sulphur and $R^w$ is $R^6$ or CN;

$R^6$ is $C_{1-6}$alkyl, $C_{2-6}$alkenyl, $C_{2-6}$alkynyl, $C_{3-6}$cycloalkyl, hydroxy$C_{1-6}$alkyl, $C_{1-6}$alkoxy, $C_{2-6}$alkenyloxy, $C_{2-6}$alkynyloxy, $CH_2F$ or $CF_3$; and $R^7$ and $R^8$ are each independently hydrogen, $C_{1-6}$alkyl, $C_{2-6}$alkenyl, $C_{2-6}$alkynyl, $C_{3-6}$cycloalkyl or $CF_3$ or $R^7$ and $R^8$, together with the nitrogen atom to which they are attached, form a 4–7 membered heteroaliphatic ring containing the nitrogen atom as the sole heteroatom;

W is selected from:

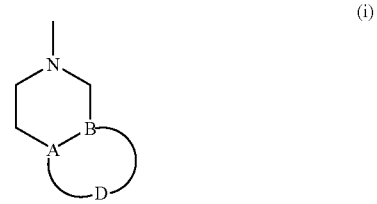

wherein A and B independently represent carbon or nitrogen, and D together with A and B completes a fused aromatic ring containing 5 or 6 atoms, 1–4 of which are nitrogen and the remainder carbon, optionally bearing up to two substituents selected from $C_{1-4}$alkyl, $C_{1-4}$alkoxy, halogen and $CF_3$;

wherein R represents H, $C_{1-4}$alkyl, phenyl or pyridyl, said phenyl and pyridyl groups optionally bearing up to three substituents selected from $C_{1-4}$alkyl, $C_{1-4}$alkoxy, halogen and $CF_3$; and (iii) L—Y—X wherein L is O, S or NR″ where R″ is H, $C_{1-6}$alkyl or $C_{3-6}$cycloalkyl;

Y is optionally branched $C_{1-4}$alkylene optionally substituted by an oxo group or Y is a group $(CH_2)_jO$ wherein the oxygen atom is nearest the group X and j is 2, 3 or 4; and X is a 5-membered heteroaromatic ring containing 1, 2, 3 or 4 heteroatoms independently chosen from oxygen, nitrogen and sulphur, at most one of the heteroatoms being oxygen or sulphur, or a 6-membered hetero aromatic ring containing 1, 2 or 3 nitrogen atoms, the 5- or 6-membered heteroaromatic ring being optionally fused to a benzene ring and the heteroaromatic ring being optionally substituted by $R^x$ and/or $R^y$ and/or $R^z$, where $R^x$ is halogen, OH, $R^3$, $OR^3$, $OCOR^3$, $NR^4R^5$, $NR^4R^5CO$, tri$(C_{1-6}$alkyl)silyl$C_{1-6}$alkoxy$C_{1-4}$alkyl, CN or $R^9$, $R^y$ is halogen, $R^3$, $OR^3$, $OCOR^3$, $NR^4R^5$, $NR^4R^5CO$ or CN and $R^z$ is $R^3$, $OR^3$ or $OCOR^3$, where $R^3$ is $C_{1-6}$alkyl, $C_{2-6}$alkenyl, $C_{2-6}$alkynyl, $C_{3-6}$cycloalkyl, hydroxy$C_{1-6}$alkyl and $R^3$ is optionally mono, di- or tri-fluorinated, $R^4$ and $R^5$ are each independently hydrogen, $C_{1-6}$alkyl, $C_{2-6}$alkenyl, $C_{2-6}$alkynyl, $C_{3-6}$cycloalkyl or $CF_3$ or, where possible, $R^4$ and $R^5$, together with a nitrogen atom to which they are commonly attached, form a 4–7 membered heteroaliphatic ring containing the said nitrogen atom and optionally one other heteroatom selected from O, N and S, and $R^9$ is benzyl or an aromatic ring containing either 6 atoms, 1, 2 or 3 of which are optionally nitrogen, or 5 atoms, 1, 2 or 3 of which are independently chosen from oxygen, nitrogen and sulphur, at most one of the atoms being oxygen or sulphur, and $R^9$ is optionally substituted by one, two or three substituents independently chosen from halogen atoms and $C_{1-4}$alkyl, $C_{2-4}$alkenyl, $C_{2-4}$alkynyl, $C_{1-4}$alkoxy, $C_{2-4}$alkenyloxy and $C_{2-4}$alkynyloxy groups each of which groups is unsubstituted or substituted by one, two or three halogen atoms, and when X is a pyridine derivative, the pyridine ring is optionally in the form of the N-oxide and providing that when X is a tetrazole derivative it is substituted by a $C_{1-4}$alkyl group; or X is phenyl optionally substituted by one, two or three groups independently selected from halogen, cyano, $C_{1-6}$alkyl, $C_{2-6}$alkenyl, $C_{2-6}$alkynyl and $C_{3-6}$cycloalkyl;

and pharmaceutically acceptable salts thereof.

6. A compound which is selected from the group consisting of:

3-(5-methylisoxazol-3-yl)-5-(1-methyl-[1H]-1,2,4-triazol-3-ylmethoxy)-1,2,3-triazolo[1,5-a]quinazoline;
3-(5-methylisoxazol-3-yl)-5-(2-methyl-[2H]-1,2,4-triazol-3-ylmethoxy)-1,2,3-triazolo[1,5-a]quinazoline;
3-(5-methylisoxazol-3-yl)-5-(1-methyl-[1H]-1,2,3-triazol-4-ylmethoxy)-1,2,3-triazolo[1,5-a]quinazoline;
3-(5-methylisoxazol-3-yl)-5-(pyridin-2-ylmethoxy)-1,2,3-triazolo[1,5-a]quinazoline;
3-(5-methylisoxazol-3-yl)-5-(pyridin-3-ylmethoxy)-1,2,3-triazolo[1,5-a]quinazoline;
3-(5-methylisoxazol-3-yl)-5-(N-oxypyridin-3-ylmethoxy)-1,2,3-triazolo[1,5-a ]quinazoline;
3-(5-methylisoxazol-3-yl)-5-[N-methyl-N-(2-methyl-[2H]-1,2,4-triazol-3-ylmethyl)amino]-1,2,3-triazolo[1,5-a]quinazoline;
3-(5-methylisoxazol-3-yl)-5-[N-methyl-N-(1-methyl-[1H]-1,2,4-triazol-3-ylmethyl)amino]-1,2,3-triazolo[1,5-a]quinazoline;
3-(5-methylisoxazol-3-yl)-5-[(2-methyl-[2H]-1,2,4-triazol-3-ylmethyl)amino]-1,2,3-triazolo[1,5-a]quinazoline;
3-(5-methylisoxazol-3-yl)-5-[(1-methyl-[1H]-1,2,4-triazol-3-ylmethyl)amino]-1,2,3-triazolo[1,5-a]quinazoline;
3-(5-methylisoxazol-3-yl)-5-(pyridin-2-ylmethylamino)-1,2,3-triazolo[1,5-a]quinazoline;
5-(isoxazol-3-ylmethylamino)-3-(5-methylisoxazol-3-yl)-1,2,3-triazolo[1,5-a ]quinazoline;
5-[(3-methyl-1,2,5-oxadiazol-4-yl)methylamino]-3-(5-methylisoxazol-3-yl)-1,2,3-triazolo[1,5-a]quinazoline;
5-(isoxazol-5-ylmethylamino)-3-(5-methylisoxazol-3-yl)-1,2,3-triazolo[1,5-α]quinazoline;
3-(5-methylisoxazol-3-yl)-5-[(5-oxo-[1H,4H]-1,2,4-triazol-3-yl)methylamino]-1,2,3-triazolo[1,5-a]quinazoline;
3-(5-methylisoxazol-3-yl)-5-[(1-methyl-[1H]-1,2,3-triazol-4-yl)methylamino]-1,2,3-triazolo[1,5-a]quinazoline;
3-(5-methylisoxazol-3-yl)-5-[N-methyl-N-(1-methyl-[1H]-1,2,3-triazol-4-ylmethyl)amino]-1,2,3-triazolo[1,5-a]quinazoline;
4-[3-(5-methylisoxazol-3-yl)-[1,2,3]triazolo[1,5-a]quinazolin-5-yl]-1H-piperazin-2-one;
4-[3-(5-methylisoxazol-3-yl)-[1,2,3]triazolo[1,5-a]quinazolin-5-yl]-1-methylpiperazin-2-one;
4-[3-(5-methylisoxazol-3-yl)-[1,2,3]triazolo[1,5-a]quinazolin-5-yl]-1-phenylpiperazin-2-one;
4-[3-(5-methylisoxazol-3-yl)-[1,2,3]triazolo[1,5-a]quinazolin-5-yl]-1-(pyridin-2-yl)piperazin-2-one;
4-[3-(5-methylisoxazol-3-yl)-[1,2,3]triazolo[1,5-a]quinazolin-5-yl]-1-(pyridin-3-yl)piperazin-2-one;
5-(5,6-dihydro-8H-imidazo[1,2-a]pyrazin-7-yl)-3-(5-methylisoxazol-3-yl)-[1,2,3]triazolo[1,5-a]quinazoline;
5-(3,4-dihydro-1H-[2,6]naphthyridin-2-yl)-3-(5-methylisoxazol-3-yl)-[1,2,3]triazolo[1,5-a]quinazoline;
5-(5,6-dihydro-8H-[1,2,4]triazolo[4,3-a]pyrazin-7-yl)-3-(5-methylisoxazol-3-yl)-[1,2,3]triazolo[1,5-a]quinazoline;

and pharmaceutically acceptable salts thereof.

7. A pharmaceutical composition comprising a compound according to claim 1 or a pharmaceutically acceptable salt thereof and a pharmaceutically acceptable excipient.

* * * * *